(12) United States Patent
Fossa

(10) Patent No.: US 6,387,894 B1
(45) Date of Patent: May 14, 2002

(54) USE OF CRF ANTAGONISTS AND RENIN-ANGIOTENSIN SYSTEM INHIBITORS

(75) Inventor: Anthony A. Fossa, Mystic, CT (US)

(73) Assignee: Pfizer Inc., New York, NY (US)

( * ) Notice: Subject to any disclaimer, the term of this patent is extended or adjusted under 35 U.S.C. 154(b) by 56 days.

(21) Appl. No.: 09/587,182

(22) Filed: Jun. 2, 2000

Related U.S. Application Data

(60) Provisional application No. 60/138,734, filed on Jun. 11, 1999.

(51) Int. Cl.[7] .................. A61K 31/55; A61K 31/505; A61K 31/41; A61K 31/40

(52) U.S. Cl. ................. 514/212.07; 514/258; 514/382; 514/423

(58) Field of Search ................... 514/212.07, 258, 514/382, 423

(56) References Cited

FOREIGN PATENT DOCUMENTS

| | | | |
|---|---|---|---|
| EP | 0773023 | 5/1997 | ......... A61K/31/435 |
| WO | WO9413643 | 6/1994 | ......... C07D/231/44 |
| WO | WO9413644 | 6/1994 | ......... C07D/231/44 |
| WO | WO9413676 | 6/1994 | ......... C07D/487/04 |
| WO | WO9413677 | 6/1994 | ......... C07D/487/04 |
| WO | WO 9533727 | 12/1995 | ......... C07D/231/12 |
| WO | WO9533750 | 12/1995 | ......... C07D/487/04 |
| WO | WO9534563 | 12/1995 | ......... C07D/471/04 |

*Primary Examiner*—Raymond Henley, III
(74) *Attorney, Agent, or Firm*—Peter C. Richardson; Gregg C. Benson; Carl J. Goddard

(57) ABSTRACT

The present invention relates to compositions and methods of achieving a therapeutic effect including, but not limited to, the treatment of congestive heart failure or hypertension in an animal, preferably a mammal including a human subject or a companion animal, using a corticotropin releasing factor (CRF) antagonist and a renin-angiotensin system (RAS) inhibitor.

26 Claims, No Drawings

USE OF CRF ANTAGONISTS AND RENIN-ANGIOTENSIN SYSTEM INHIBITORS

This application is filed claiming priority from Provisional Application No. 60/138,734 filed Jun. 11, 1999.

BACKGROUND OF THE INVENTION

The present invention relates to compositions and methods of achieving a therapeutic effect including the treatment of congestive heart failure or hypertension in an animal, preferably a mammal including a human subject or a companion animal, using a corticotropin releasing factor (CRF) antagonist, preferably in synergistic combination with a renin-angiotensin system (RAS) inhibitor.

In preferred embodiments of the compositions and methods of this invention, the CRF antagonists comprise compounds of structural formula I or II, including the pharmaceutically acceptable salts thereof, as defined hereinbelow.

The compounds of formula I or II, their pharmaceutically acceptable salts, and methods of preparing such compounds and salts are disclosed in commonly assigned PCT publication numbers WO 95/34563, WO 95/33750, WO 94/13676, WO 94/13677 and European patent application number EP 773 023. Each of the applications corresponding to PCT publication numbers WO 95/34563, WO 95/33750, WO 94/13676 and WO 94/13677 designate, inter alia, the United States and are incorporated herein by reference in their entirety.

The foregoing PCT and EP publications refer to the use of the compounds of formula I or II, and their pharmaceutically acceptable salts, in the treatment of illnesses induced or facilitated by CRF and in the treatment of anxiety, cardiovascular diseases, depression, fatigue syndrome, gastrointestinal diseases, headache, pain, cancer, immune dysfunction, hemorrhagic stress, drug addiction, drug and alcohol withdrawal symptoms, fertility problems, stress-induced psychotic episodes, neurodegenerative diseases such as Alzheimer's disease; irritable bowel syndrome including Crohn's disease, spastic colon and irritable colon; eating disorders such as anorexia nervosa; and inflammatory disorders such as arthritis, asthma and allergies. Other CRF antagonists useful in the compositions and methods of this invention are referred to in commonly assigned PCT publication numbers WO 95/33727, WO 94/13644 and WO 94/13643. Each of the applications corresponding to PCT publication numbers WO 95/33727, WO 94/13644 and WO 94/13643 designate, inter alia, the United States and are incorporated herein by reference in their entirety.

RAS inhibitors useful in the practice of the instant invention include renin inhibitors, angiotensin-converting enzyme (ACE) inhibitors, and angiotensin-II (A-II) antagonists. Such RAS inhibitors are useful in the lowering of blood pressure in mammals and find utility in the treatment of congestive heart failure as well as other therapeutic effects. Specific RAS inhibitors useful in the practice of the instant invention are disclosed and referenced in detail hereinbelow.

Until the invention described herein, there was no report of use of or intent to use a CRF antagonist together with a RAS inhibitor to achieve any therapeutic effect including the synergistic treatment of congestive heart failure or hypertension.

Further, until this invention, there was no report of a pharmaceutical composition comprising a CRF antagonist together with a RAS inhibitor, nor of the use or intent to use such a composition in the synergistic therapeutic treatment of any condition including congestive heart failure or hypertension.

SUMMARY OF THE INVENTION

This invention relates to compositions and methods useful in achieving therapeutic effects such as the synergistic treatment of congestive heart failure or hypertension, which compositions preferably comprise synergistic therapeutically effective amounts of a CRF antagonist, a RAS inhibitor and a pharmaceutically acceptable carrier or diluent and which methods preferably comprise administering to an animal, preferably a mammal including a human subject or a companion animal in need of such treatment, synergistic therapeutically effective amounts of a CRF antagonist and a RAS inhibitor.

Preferably, the invention relates to the use of a CRF antagonist in combination with a RAS inhibitor selected from the group consisting of an angiotensin-converting enzyme (ACE) inhibitor, an angiotensin II antagonist and a renin inhibitor. More preferably, the renin angiotensin system inhibitor is a compound selected from the group consisting of benazeprilat, captopril, enalapril, lisinopril, losartan, valsartan, irbesartan, candesartan, telmisartan, tasosartan and eprosartan.

A preferred class of CRF antagonists comprises compounds of structural formula I or II, below,

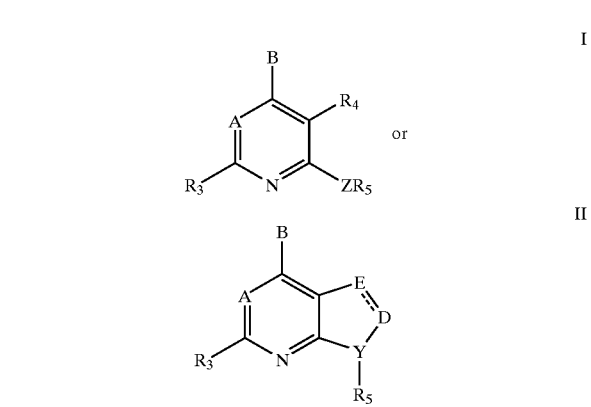

including the pharmaceutically acceptable salts thereof, wherein the dashed line represents an optional double bond, and A, B, D, E, Y, Z, $R_3$, $R_4$ and $R_5$ are as defined hereinbelow.

DETAILED DESCRIPTION OF THE INVENTION

The present invention relates to compositions and methods of achieving a therapeutic effect including, but not limited to, the treatment of congestive heart failure or hypertension in an animal, preferably a mammal including a human subject or a companion animal, using a corticotropin releasing factor (CRF) antagonist, preferably in synergistic combination, with a renin-angiotensin system (RAS) inhibitor.

A first preferred aspect of the instant invention relates to compositions and methods for treating congestive heart failure, which compositions comprise synergistically effective amounts of a CRF antagonist, a RAS inhibitor and a pharmaceutically acceptable carrier or diluent and which methods comprise administering to an animal, preferably a mammal including a human subject or a companion animal, such as a dog or cat, in need of such treatment, synergistic therapeutically effective amounts of a CRF antagonist and a RAS inhibitor.

A second preferred aspect of the instant invention relates to compositions and methods for treating hypertension, which compositions comprise synergistically effective amounts of a CRF antagonist and a RAS inhibitor, and a pharmaceutically acceptable carrier or diluent and which methods comprise administering to an animal, preferably a mammal including a human subject or a companion animal, such as a dog or cat, in need of such treatment, synergistic therapeutically effective amounts of a CRF antagonist and a RAS inhibitor.

The term "synergistic" as utilized herein means that the effect achieved with the methods and compositions of the instant invention is greater than the sum of the effects that result from methods and compositions comprising the inhibitors and antagonists of this invention separately and in the amounts employed in the methods and compositions hereof.

The term corticotropin releasing factor (CRF) antagonist refers to a compound having the ability to inhibit or reverse the deleterious effects of the presence of CRF. It is well known that CRF profoundly stimulates the pituitary-adrenalcortical axis and, in dysfunctional states, initiates behavioral, physiological and endocrine responses that are essentially identical to those observed when animals, including humans and companion animals, are subjected to a stressful environment. Therefore, CRF antagonists are known to have utility, inter alia, in the amelioration of certain stress-induced conditions including memory loss, mood alteration, depression, hypertension and the like.

The importance of CRF antagonists is set out h the literature, e.g., as discussed in U.S. Pat. No. 5,063,245, which is incorporated herein by reference, and a recent outline of the different activities possessed by CRF antagonists is found in Pharm. Rev., 43, 425–473 (1991). Such activity is readily determined by one skilled in the art according to standard assays including the methods described in Endocrinology, 116, 1653–1659 (1985) and Peptides, 10, 179–188 (1989) which determine the binding affinity of a test compound for a CRF receptor. The binding affinities for the active compounds, expressed as $IC_{50}$ values, generally range from about 0.2 nanomolar to about 10 micromolar. A variety of additional compounds having utility as CRF antagonists are, or will be, known to those skilled in the art. For example, CRF antagonists are mentioned in U.S. Pat. Nos. 4,605,642 and 5,063,245 referring to certain peptides and pyrazolinones, respectively, the teachings of which are incorporated herein by reference.

In the practice of the instant invention, any CRF antagonist may be employed. A preferred class of CRF antagonists comprises compounds having the structural formula I or II shown and described hereinbelow,

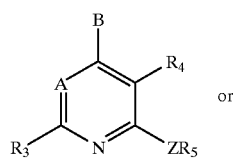

I

-continued

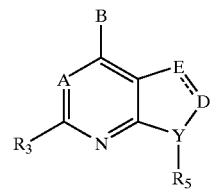

II including the pharmaceutically acceptable salts thereof, wherein the dashed line represents an optional double bond;

A is —$CR_7$ or N;

B is —$NR_1R_2$, —$CR_1R_2R_{11}$, —$C(=CR_1R_{12})R_2$, —$NHCR_{11}R_1R_2$, —$OCR_{11}R_1R_2$, —$SCR_{11}R_1R_2$, —$CR_{11}R_2OR_1$, —$CR_{11}R_2SR_1$, —$C(S)R_2$, —$NHNR_1R_2$, —$CR_2R_{11}NHR_1$ or —$C(O)R_2$;

D is: (i) N or —$CR_{10}$ when a double bond connects E and D and E is —$CR_4$; (ii) —$CR_{10}$ when a double bond connects E and D and E is N; (iii) —$CR_8R_9$, —$CHR_{10}$, —C=O, —C=S, —C=NH, or —$C=NCH_3$ when a single bond connects E and D;

E is —$CR_4$ or N when a double bond connects E and D, and E is —$CR_4R_6$ or —$NR_6$ when a single bond connects E and D;

Y is N or —CH;

Z is NH, O, S, —$N(C_1-C_2$ alkyl) or —$CR_{12}R_{13}$, wherein $R_{12}$ and $R_{13}$ are each, independently, hydrogen, trifluoromethyl or methyl, or one of $R_{12}$ and $R_{13}$ is cyano and the other is hydrogen or methyl;

$R_1$ is hydrogen or $C_1$–$C_6$ alkyl which is optionally substituted with one or two substituents independently selected from hydroxy, cyano, nitro, fluoro, chloro, bromo, iodo, $CF_3$, $C_1$–$C_4$ alkoxy, —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —NH($C_1$–$C_4$ alkyl), —N($C_1$–$C_2$ alkyl)($C_1$–$C_4$ alkyl), —S($C_1$–$C_4$ alkyl), —N($C_1$–$C_4$alkyl)CO($C_1$–$C_4$ alkyl), —NHCO($C_1$–$C_4$ alkyl), —$CO_2$($C_1C_4$ alkyl), —CONH($C_1$–$C_4$ alkyl), —CON($C_1$–$C_4$ alkyl)($C_1$–$C_2$ alkyl), ($C_1$–$C_4$ alkyl) sulfinyl, ($C_1$–$C_4$ alkyl)sulfonyl, and ($C_1$–$C_4$ alkyl) sulfanyl, and wherein said $C_1$–$C_6$ alkyl, $C_1$–$C_4$ alkoxy and the $C_1$–$C_4$ alkyl moieties in the foregoing $R_1$ groups optionally contain one double or triple bond;

$R_2$ is $C_1$–$C_6$ alkyl, heteroaryl, aryl, (heteroaryl)$C_1$–$C_4$ alkyl or (aryl)$C_1$–$C_4$ alkyl wherein said aryl and the aryl moiety of said (aryl)$C_1$–$C_4$ alkyl are selected from the group consisting of phenyl and naphthyl, and said heteroaryl and the heteroaryl moiety of said (heteroaryl)$C_1$–$C_4$ alkyl is selected from the group consisting of thienyl, benzothienyl, pyridyl, quinolyl, pyrazinyl, pyrimidyl, imidazolyl, furanyl, benzofuranyl, benzothiazolyl, isothiazolyl, thiazolyl, benzisothiazolyl, benzisoxazolyl, benzimidazolyl, indolyl, and benzoxazolyl; or $R^2$ is $C_3$–$C_8$ cycloalkyl or ($C_3$–$C_8$ cycloalkyl)$C_1$–$C_6$ alkyl, wherein one or two of the ring carbons of said cycloalkyl having at least 4 ring members and the cycloalkyl moiety of said ($C_3$–$C_8$ cycloalkyl)$C_1$–$C_6$ alkyl having at least 4 ring members is optionally replaced by an oxygen or sulfur atom or by —$NR_{14}$ wherein $R_{14}$ is hydrogen or $C_1$–$C_4$ alkyl; and wherein each of the foregoing $R_2$ groups is optionally substituted by from one to three substituents independently selected from chloro, fluoro and $C_1$–$C_4$ alkyl, or by one substituent selected from bromo, iodo, cyano, nitro, $C_1$–$C_6$ alkoxy, —O—CO—($C_1$–$C_4$ alkyl), —O—CO—N($C_1$–$C_4$ alkyl)($C_1$–$C_2$ alkyl), —$CO_2$ ($C_1$–$C_4$ alkyl), ($C_1$–$C_4$ alkyl)sulfanyl, ($C_1$–$C_4$ alkyl)sulfinyl, and ($C_1$–$C_4$ alkyl)sulfonyl, and wherein said $C_1$–$C_6$ alkyl and the $C_1$–$C_4$ alkyl and $C_1$–$C_6$ alkyl moieties of the foregoing $R_2$ groups optionally contain one carbon—carbon double or triple bond;

or $R^1$ and $R^2$ of said —$NR_1R_2$ and said —$CR_1R_2R_{11}$ are taken together to form a saturated 5 to 8 member ring, wherein said ring optionally contains one or two carbon—carbon double bonds, and wherein one or two of the ring carbons is optionally replaced by a heteroatom selected from O, S and N;

$R_3$ is hydrogen, $C_1$–$C_6$ alkyl, fluoro, chloro, bromo, iodo, hydroxy, amino, SH, —NH($C_1$–$C_4$ alkyl), —N($C_1$–$C_4$ alkyl)($C_1$–$C_2$ alkyl), —$CH_2OH$, —$CH_2OCH_3$, —O($C_1$–$C_4$ alkyl), ($C_1$–$C_4$ alkyl)sulfanyl, ($C_1$–$C_4$ alkyl)sulfonyl, or ($C_1$–$C_4$ alkyl)sulfinyl, wherein said $C_1$–$C_6$ alkyl and the $C_1$–$C_4$ alkyl moieties of the foregoing $R_3$ groups optionally contain one double or triple bond and are optionally substituted by from one to three substituents independently selected from hydroxy, amino, $C_1$–$C_3$ alkoxy, —NH($C_1$–$C_2$ alkyl), —N($C_1$–$C_2$ alkyl)$_2$, —$NHCOCH_3$, fluoro, chloro and $C_1$–$C_3$ thioalkyl;

$R_4$ is hydrogen, $C_1$–$C_6$ alkyl, fluoro, chloro, bromo, iodo, $C_1$–$C_6$ alkoxy, formyl, trifluoromethoxy, —$CH_2OCH_3$, —$CH_2OCH_2CH_3$, —$CH_2CH_2OCH_3$, —$CH_2CF_3$, $CF_3$, amino, nitro, —NH($C_1$–$C_4$ alkyl), —N($CH_3$)$_2$, —$NHCOCH_3$, —$NHCONHCH_3$, ($C_1$–$C_4$ alkyl)sulfanyl, ($C_1$–$C_4$ alkyl)sulfinyl, ($C_1$–$C_4$ alkyl)sulfonyl, cyano, hydroxy, —CO($C_1$–$C_4$ alkyl), —CHO, or —$CO_2$($C_1$–$C_4$ alkyl), wherein said $C_1$–$C_6$ alkyl, $C_1$–$C_6$ alkoxy and the $C_1$–$C_4$ alkyl moieties of the foregoing $R_4$ groups optionally contain one double or triple bond and are optionally substituted with one substituent selected from hydroxy, amino, —$NHCOCH_3$, —NH($C_1$–$C_2$ alkyl), —N($C_1$–$C_2$ alkyl)$_2$, —$CO_2$($C_1$–$C_4$ alkyl), —CO($C_1$–$C_4$ alkyl), $C_1$–$C_3$ alkoxy, ($C_1$–$C_3$ alkyl)sulfanyl, fluoro, chloro, cyano and nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 3- to 8-membered cycloalkyl or 9- to 12-membered bicycloalkyl, wherein said cycloalkyl and bicycloalkyl optionally contain one or two of O, S or —N—G wherein G is hydrogen, $C_1$–$C_4$ alkyl, $C_1$–$C_4$ alkanoyl, phenyl or benzyl, wherein each of the above $R_5$ groups is optionally substituted by from one to three substituents independently selected from fluoro, chloro, $C_1$–$C_6$ alkyl, $C_1$–$C_6$ alkoxy and trifluoromethyl, or one substituent selected from bromo, iodo, cyano, nitro, amino, —NH($C_1$–$C_4$ alkyl), —N($C_1$–$C_4$ alkyl)($C_1$–$C_2$ alkyl), —$CO_2$($C_1$–$C_4$ alkyl), —CO($C_1$–$C_4$ alkyl), —$SO_2NH$($C_1$–$C_4$ alkyl), —$SO_2N$($C_1$–$C_4$ alkyl)($C_1$–$C_2$ alkyl), —$SO_2NH_2$, —$NHSO_2$($C_1$–$C_4$ alkyl), —S($C_1$–$C_4$ alkyl), and —$SO_2$($C_1$–$C_4$ alkyl), wherein said $C_1$–$C_4$ alkyl and $C_1$–$C_6$ alkyl moieties of the foregoing $R_5$ groups optionally contain one double or triple bond and are optionally substituted by one or two substituents independently selected from fluoro, chloro, hydroxy, amino, methylamino, dimethylamino and acetyl;

$R_6$ is hydrogen or $C_1$–$C_8$ alkyl, wherein said $C_1$–$C_6$ alkyl is optionally substituted by a single hydroxy, methoxy, ethoxy or fluoro group;

$R_7$ is hydrogen, $C_1$–$C_4$ alkyl, fluoro, chloro, bromo, iodo, cyano, hydroxy, $C_1$–$C_4$ alkoxy, —CO($C_1$–$C_4$ alkyl), —$CO_2$($C_1$–$C_4$ alkyl), —$OCF_3$, $CF_3$, —$CH_2OH$, —$CH_2OCH_3$ or —$CH_2OCH_2CH_3$;

$R_8$ and $R_9$ are each, independently, hydrogen, hydroxy, methyl, ethyl, methoxy, or ethoxy;

or $R_8$ and $R_9$ together form an oxo (=O) group;

$R_{10}$ is hydrogen, $C_1$–$C_6$ alkyl, fluoro, chloro, bromo, iodo, $C_1$–$C_6$ alkoxy, formyl, amino, —NH($C_1$–$C_4$ alkyl), —N($C_1$–$C_4$ alkyl)($C_1$–$C_2$ alkyl), —$SO_n$($C_1$–$C_4$ alkyl), wherein n is 0, 1 or 2, cyano, carboxy, or amido, wherein said $C_1$–$C_6$ alkyl and the $C_1$–$C_4$ alkyl moieties of the foregoing $R_{10}$ groups are optionally substituted by one of hydroxy, trifluoromethyl, amino, carboxy, amido, —NHCO($C_1$–$C_4$ alkyl), —NH($C_1$–$C_4$ alkyl), —N($C_1$–$C_4$ alkyl)($C_1$–$C_2$ alkyl), —$CO_2$($C_1$–$C_4$ alkyl), $C_1$–$C_3$ alkoxy, $C_1$–$C_3$ thioalkyl, fluoro, bromo, chloro, iodo, cyano or nitro; and $R_{11}$ is hydrogen, hydroxy, fluoro, or methoxy.

The term "alkyl", as used herein, unless otherwise indicated, includes saturated monovalent hydrocarbon radicals having straight or branched moieties or combinations thereof.

The term "alkoxy", as used herein, unless otherwise indicated, includes O-alkyl groups wherein "alkyl" is defined above.

The term "treatment", as used herein, unless otherwise indicated, includes the treatment, prevention, or inhibition of any disorder enumerated within the methods of the invention.

More specific compounds for use in the compositions and methods of the invention include compounds of formula I or II, or pharmaceutically acceptable salts thereof, wherein: B is —$NR_1R_2$, —$NHCHR_1R_2$, —$CR_1R_2R_{11}$, —$SCHR_1R_2$ or —$OCHR_1R_2$; $R_1$ is $C_1$–$C_6$ alkyl which is optionally substituted with a single hydroxy, fluoro or $C_1$–$C_2$ alkoxy group and optionally contains one carbon—carbon double or triple bond; $R_2$ is benzyl or $C_1$–$C_6$ alkyl which optionally contains one carbon—carbon double or triple bond, wherein said $C_1$–$C_6$ alkyl and the phenyl moiety of said benzyl are optionally substituted with fluoro, $C_1$–$C_2$ alkyl, or $C_1$–$C_2$ alkoxy; and $R_{11}$ is hydrogen or fluoro.

Other more specific compounds for use in the compositions and methods of the invention include compounds of formula I or II, or pharmaceutically acceptable salts thereof, wherein $R_2$ is (aryl)$C_1$–$C_4$ alkyl or (heteroaryl)$C_1$–$C_4$ alkyl in which said aryl or heteroaryl moiety is phenyl, thienyl, benzofuranyl, furanyl, benzothienyl, thiazolyl, pyridyl or benzothiazolyl.

Other more specific compounds for use in the compositions and methods of the invention include compounds of formula I or II, or pharmaceutically acceptable salts thereof, wherein B is —$NR_1R_2$ or —$CHR_1R_2$ in which $R_1$ and $R_2$ are taken together with N or CH to form a 5- or 6-membered ring optionally having sulfur, oxygen, or one more nitrogen atoms in said ring, such as a pyrrolidinyl, pyrrolyl, pyrazolyl, imidazolyl, oxazolyl, thiazolyl, isoxazolyl, thiadiazolyl, oxadiazolyl, pyridyl, pyrazinyl or pyrimidyl group.

Other more specific compounds for use in the compositions and methods of the invention include compounds of formula I or II, or pharmaceutically acceptable salts thereof, wherein B is —$NHCHR_1R_2$ or —$OCHR_1R_2$, wherein the $CHR_1R_2$ moiety is a 5- or 6-membered ring which optionally contains one oxygen or sulfur, such as a tetrahydrofuranyl, tetrahydrothiafuranyl or cyclopentanyl group.

Other more specific compounds for use in the compositions and methods of the invention include compounds of formula I or II, or pharmaceutically acceptable salts thereof, wherein B is tetrahydrofuranyl, tetrahydrothiafuranyl, tetrahydrothienyl, thiazolidinyl or cyclopentanyl.

Other more specific compounds for use in the compositions and methods of the invention include compounds of formula I or II, or pharmaceutically acceptable salts thereof, wherein $R_3$ is methyl, chloro, or methoxy; $R_4$ is methyl, —$CH_2OH$, cyano, trifluoromethoxy, methoxy, trifluoromethyl, chloro, —$CO_2CH_3$, —$CH_2OCH_3$, —$CH_2Cl$, —$CH_2F$, amino, nitro, hydrogen, methylsulfinyl, methylsulfanyl, methylsulfonyl, or ethyl; and $R_5$ is phenyl or pyridyl wherein said phenyl or pyridyl is substituted by one substituent independently selected from fluoro, chloro, bromo, iodo, $C_1$–$C_{14}$ alkoxy, trifluoromethyl, $C_1$–$C_3$ hydroxyalkyl, hydroxy, formyl, —$CO_2(C_1$–$C_2$ alkyl), (amino)$C_1$–$C_2$ alkyl, —$CO(C_1$–$C_4$ alkyl), and $C_1$–$C_6$ alkyl, wherein said $C_1$–$C_6$ alkyl and said $C_1$–$C_4$ alkyl are optionally substituted by a single hydroxy, or fluoro group and optionally contains one carbon—carbon double or triple bond.

For use in the compositions and methods of the invention, specific compounds of formula I or II include:

- 4-(1-ethyl-propoxy)-2,5-dimethyl-6-(2,4,6-trimethyl-benzyl)-pyrimidine;
- 2-(4-bromo-2,6-dimethyl-phenoxy)-4-(1-ethyl-propoxy)-3,6-dimethyl-pyridine;
- 2-(4-ethyl-2,6-dimethyl-phenoxy)-4-(1-ethyl-propoxy)-3,6-dimethyl-pyridine;
- 3-ethyl-4-(1-ethyl-propoxy)-6-methyl-2-(2,4,6-trimethyl-phenoxy)-pyridine;
- 2-(2,6-dimethyl-4-propyl-phenoxy)-4-(1-ethyl-propoxy)-3,6-dimethyl-pyridine;
- 4-(1-ethyl-propoxy)-2-(4-methoxy-2,6-dimethyl-phenoxy)-3,6-dimethyl-pyridine;
- 2-(4-ethoxy-2,6-dimethyl-phenoxy)-4-(1-ethyl-propoxy)-3,6-dimethyl-pyridine;
- 2-(4-chloro-2,6-dimethyl-phenoxy)-4-(1-ethyl-propoxy)-3,6-dimethyl-pyridine;
- 4-(1-methoxymethyl-propoxy)-3,6-dimethyl-2-(2,4,6-trimethyl-phenoxy)-pyridine;
- [3,6-dimethyl-2-(2,4,6-trimethyl-phenoxy)-pyridin-4-yl]-diethyl-amine;
- [3,6-dimethyl-2-(2,4,6-trimethyl-phenoxy)-pyridin-4-yl]-ethyl-propyl-amine;
- [2,5-dimethyl-6-(2,4,6-trimethyl-phenoxy)-pyrimidin-4-yl](1-ethyl-propyl)-amine;
- butyl-[3,6-dimethyl-2-(2,4,6-trimethyl-phenoxy)-pyridin-4-yl]-ethyl-amine;
- 4-(1-ethyl-propoxy)-3,6-dimethyl-2-(2,4,6-trimethyl-phenylsulfanyl)-pyridine;
- butyl-[2-(4-chloro-2,6-dimethyl-phenoxy)-3,6-dimethyl-pyridin-4-yl]-ethyl-amine;
- 4-(1-ethyl-propylamino)-6-methyl-2-(2,4,6-trimethyl-phenoxy)-nicotinic acid methyl ester;
- [3,6-dimethyl-2-(2,4,6-trimethyl-phenylsulfanyl)-pyridin-4-yl]-ethyl-propyl-amine;
- [4-(1-ethyl-propylamino)-6-methyl-2-(2,4,6-trimethyl-phenoxy)-pyridin-3-yl]-methanol;
- [2-(4-chloro-2,6-dimethyl-phenoxy)-3,6-dimethyl-pyridin-4-yl]-ethyl-propyl-amine;
- 1-(ethyl-propyl)-[6-methyl-3-nitro-2-(2,4,6-trimethyl-phenoxy)-pyridin-4-yl]-amine;
- N4-(1-ethyl-propyl)-6-methyl-3-nitro-N2-(2,4,6-trimethyl-phenyl)-pyridine-2,4-diamine;
- N4-(1-ethyl-propyl)-6-methyl-2-(2,4,6-trimethyl-phenoxy)-pyridine-3,4-diamine;
- N4-(1-ethyl-propyl)-6-methyl-N2-(2,4,6-trimethyl-phenyl)-pyridine-2,3,4-triamine;
- [3,6-dimethyl-2-(2,4,6-trimethyl-phenoxy)-pyridin-4-yl]-ethyl-(2,2,2-trifluoro-ethyl)-amine;
- [3-chloromethyl-6-methyl-2-(2,4,6-trimethyl-phenoxy) pyridin-4-yl]-(1-ethyl-propyl)-amine;
- [3,6-dimethyl-2-(2,4,6-trimethyl-phenoxy)-pyridin-4-yl]-(1-ethyl-propyl)-amine;
- (1-ethyl-propyl)-[2-methyl-5-nitro-6-(2,4,6-trimethyl-pyridin-3-yloxy)-pyrimidin-4-yl]-amine;
- (1-ethyl-propyl)-[3-methoxymethyl-6-methyl-2-(2,4,6-trimethyl-phenoxy)-pyridin-4-yl]-amine;
- N-(1-ethyl-propyl)-2-methyl-5-nitro-N-(2,4,6-trimethyl-pyridin-3-yl)-pyrimidine-4,6-diamine;
- [2-(4-chloro-2,6-dimethyl-phenoxy)-3,6-dimethyl-pyridin-4-yl]-diethyl-amine;
- 4-(1-ethyl-propoxy)-3,6-dimethyl-2-(2,4,6-trimethylphenoxy)-pyridine;
- butyl-[2,5-dimethyl-7-(2,4,6-trimethylphenyl)-6,7-dihydro-5H-pyrrolo[2,3-d]pyrimidin-4-yl]-ethyl-amine;
- 4-(butyl-ethylamino)-2,5-dimethyl-7-(2,4,6-trimethylphenyl)-5,7-dihydro-pyrrolo[2,3-d]pyrimidin-6-one;
- 4-(1-ethylpropoxy)-2,5-dimethyl-6-(2,4,6-trimethylphenoxy)-pyrimidine;
- N-butyl-N-ethyl-2,5-dimethyl-N-(2,4,6-trimethylphenyl)-pyrimidine-4,6-diamine;
- (1-ethyl-propyl)-[5-methyl-3-(2,4,6-trimethyl-phenyl)-3H-imidazo[4,5-b]pyridin-7-yl]-amine;
- [2,5-dimethyl-3-(2,4,6-trimethyl-phenyl)-3H-imidazo[4,5-b]pyridin-7-yl]-(1-ethyl-propyl)-amine;
- N4-(1-ethyl-propyl)-6,N3-dimethyl-2-(2,4,6-trimethyl-phenoxy)-pyridine-3,4-diamine;
- N4-(1-ethyl-propyl)-6,N3,N3-trimethyl-2-(2,4,6-trimethyl-phenoxy)-pyridine-3,4-diamine;
- 6-(1-ethyl-propoxy)-2-methyl-N4-(2,4,6-trimethyl-phenyl)-pyrimidine-4,5-diamine;
- [4-(1-ethyl-propoxy)-3,6-dimethyl-pyridin-2-yl]-(2,4,6-trimethylphenyl)-amine;
- 6-(ethyl-propyl-amino)-2,7-dimethyl-9-(2,4,6-trimethylphenyl)-7,9-dihydro-purin-8-one; and the pharmaceutically acceptable salts thereof.

For use in the compositions and methods of the invention, specific compounds of formula II wherein E and D are connected by a double bond, E is —$CR_4$, D is —$CR_{10}$ or N, Y is N, and A is —$CR_7$, include:

- butyl-[3,6-dimethyl-1-(2,4,6-trimethylphenyl)-1H-pyrazolo[3,4-b]pyridin-4-yl]-ethylamine;
- 3,6-dimethyl-4-(tetrahydrofuran-3-yloxy)-1-(2,4,6-trimethylphenyl)-1H-pyrazolo[3,4-b]pyridine;
- [3,6-dimethyl-1-(2,4,6-trimethylphenyl)-1H-pyrazolo[3,4,b]pyridin-4-yl]-(1-methoxymethylpropyl)-amine;
- 4-(1-methoxymethylpropoxy)-3,6-dimethyl-1-(2,4,6-trimethylphenyl)-1H-pyrazolo[3,4-b]pyridine;
- (1-ethylpropyl)-[3,5,6-trimethyl-1-(2,4,6-trimethylphenyl)-1H-pyrazolo[3,4-b]pyridin-4-yl]-amine;

4-(1-ethylpropoxy)-2,5-dimethyl-7-(2,4,6-trimethylphenyl)-7H-pyrrolo[2,3-b]pyridine;

4-(1-ethylpropoxy)-2,5,6-trimethyl-7-(2,4,6-trimethylphenyl)-7H-pyrrolo[2,3-b]pyridine;

4-(1-ethylpropoxy)-2,5-dimethyl-7-(2,6-dimethyl-4-bromophenyl)-7H-pyrrolo[2,3-b]pyridine; and the pharmaceutically acceptable salts thereof.

For use in the compositions and methods of the invention specific compounds of formula II wherein E and D are connected by a double bond, E is —$CR_4$, and D, Y and A are N, include:

3-{(4-methyl-benzyl)-[3,6-dimethyl-1-(2,4,6-trimethylphenyl)-1H-pyrazolo[3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo[3,4-d]pyrimidin-4-yl]-amino}-ethanol;

dibutyl-[6-methyl-3-methylsulfanyl-1-(2,4,6-trichlorophenyl)-1H-pyrazolo[3,4-d ]pyrimidin-4-yl}-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfonyl-1-(2,4,6-trichlorophenyl)-1H-pyrazolo[3,4-d]pyrimidin-4-yl]-amine;

butyl-cyclopropylmethyl-[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo[3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-3-methylsulfanyl-1-(2,4,6trimethylphenyl)-1H-pyrazolo[3,4-d]pyrimidine;

2-[3,6-dimethyl-1-(2,4,6-trimethylphenyl)-1H-pyrazolo[3,4-d]pyrimidin-4-ylamine]-butan-1-ol;

[3,6-dimethyl-1-(2,4,6-trimethylphenyl)-1H-pyrazolo-[3,4-d]pyrimidin-4-yl]-(1-methylpropyl)amine;

4-(1-methoxymethylpropoxy)-3,6-dimethyl-1-(2,4,6-trimethylphenyl)-1H-pyrazolo[3,4-d]pyrimidine; and the pharmaceutically acceptable salts thereof.

For use in the compositions and methods of the invention, specific compounds of formula II wherein E and D are connected by a double bond, E is —$CR_4$, D is —$CR_{10}$, and Y and A are N, include:

n-butyl-ethyl-[2,5-dimethyl-7-(2,4,6-trimethylphenyl)-7H-pyrrolo[2,3-d]pyrimidin-4-yl]amine;

di-n-propyl-[2,5-dimethyl-7-(2,4,6-trimethylphenyl)-7H-pyrrolo[2,3-d]pyrimidin-4-yl]amine;

ethyl-n-propyl-[2,5-dimethyl-7-(2,4,6-trimethylphenyl)-7H-pyrrolo[2,3-d]pyrimidin-4-yl]amine;

diethyl-2,5-dimethyl-7-(2,4,6-trimethylphenyl)-7H-pyrrolo[2,3-d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine;

2-{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo[2,3-d]pyrimidine;

n-butyl-ethyl-[2,5-dimethyl-7-(2,4-dimethylphenyl)-7H-pyrrolo[2,3-d]pyrimidin-4-yl]amine;

2,5-dimethyl-7-(2,4,6-trimethylphenyl)-7H-pyrrolo[2,3-d]pyrimidyl-4-yl]-(1-ethyl-propyl)amine;

2-[7-(4-bromo-2,6-dimethylphenyl)-2,5-dimethyl-7H-pyrrolo[2,3-d]pyrimidin-4-ylamino]-butan-1-ol 2-(S)-[7-(4-bromo-2,6-dimethylphenyl)-2,5-dimethyl-7H-pyrrolo[2,3-d]pyrimidin-4-ylamino]-butan-1-ol;

4-(1-ethyl-propoxy)-2,5,6-trimethyl-7-(2,4,6-trimethylphenyl)-7H-pyrrolo[2,3-d]pyrimidine;

4-(1-methoxymethyl-propoxy)-2,5,6-trimethyl-7-(2,4,6-trimethylphenyl)-7H-pyrrolo[2,3-d]pyrimidine;

4-(1-ethyl-butyl)-2,5,6-trimethyl-7-(2,4,6-trimethylphenyl)-7H-pyrrolo-[2,3-d]pyrimidine;

[7-(4-bromo-2,6-dimethyl-phenyl)-2,5-dimethyl-7H-pyrrolo[2,3-d]pyrimidin-4-yl]-(1-methoxymethyl-propyl)-amine;

2-[7-(2-bromo-4,6-dimethyl-phenyl)-2,5-dimethyl-7H-pyrrolo[2,3-d]pyrimidin-4-ylamino]-butan-1-ol;

2-[7-(4-ethyl-2,6-dimethyl-phenyl)-2,5-dimethyl-7H-pyrrolo[2,3-d]pyrimidin-4-ylamino]-butan-1-ol;

2-[7-(2-ethyl-4,6-dimethylphenyl)-2,5-dimethyl-7H-pyrrolo[2,3-d]pyrimidin-4-ylamino]-butan-1-ol;

2-[7-(2-fluoromethyl-4,6-dimethylphenyl)-2,5-dimethyl-7H-pyrrolo[2,3-d]pyrimidin-4-ylamino]-butan-1-ol;

and the pharmaceutically acceptable salts thereof.

The compounds of formula I or II, and their pharmaceutically acceptable salts, are readily prepared. The compounds of formula II wherein A, D and Y are N, a double bond connects E and D, and E is —$CR_4$, are prepared by one or more of the synthetic methods disclosed in PCT publication number WO 94/13677, referred to hereinabove and incorporated herein by reference. The compounds of formula II wherein A and Y are N, a double bond connects E and D, E is —$CR_4$, and D is —$CR_{10}$, are prepared by one or more of the synthetic methods disclosed in PCT publication number WO 94/13676, referred to hereinabove and incorporated herein by reference. The compounds of formula II wherein A is —$CR_7$, a double bond connects E and D, E is —$CR_4$, D is N or —$CR_{10}$, and Y is N, are prepared by one or more of the synthetic methods disclosed in PCT publication number WO 95/34563, referred to hereinabove and incorporated herein by reference. The remaining compounds of formula II and the compounds of formula I are prepared by one or more of the synthetic methods disclosed in PCT publication number WO 95/33750, referred to hereinabove and incorporated herein by reference.

Pharmaceutically acceptable salts of the compounds of formula I or II include salts of acidic or basic groups. For example, pharmaceutically acceptable salts include sodium, calcium and potassium salts of acidic groups, such as when the $R_{10}$ substituent is carboxy. Such salts are generally prepared by combining a compound of formula I or II with one molar equivalent of a suitable $Na^+$, $K^+$, or $Ca^{+2}$ counterion in a suitable solvent. Pharmaceutically acceptable acid addition salts of basic groups, such as amino groups, are formed by reacting the base form of a compound of formula I or II with an appropriate conjugate acid. Pharmaceutically acceptable salts of basic groups include hydrochloride, hydrobromide, sulfate, hydrogen sulfate, phosphate, hydrogen phosphate, dihydrogen phosphate, acetate, succinate, citrate, tartrate, lactate, mandelate, benzenesulfonate (besylate), methanesulfonate (mesylate) and p-toluenesulfonate (tosylate) salts. When the salt is of a monobasic acid (e.g., the hydrochloride, the hydrobromide, the p-toluenesulfonate, the acetate), at least one molar equivalent and usually a molar excess of the acid is employed. However, when such salts as the sulfate, the hemisuccinate, the hydrogen phosphate or the phosphate are desired, the appropriate and exact chemical equivalents of the conjugate acid will generally be used. The free base and the acid are usually combined in a co-solvent from which the desired salt precipitates, or can be otherwise advantageously isolated by concentration or addition of a non-solvent.

In the practice of the instant invention, the CRF antagonist is preferably used in synergistic combination with a RAS inhibitor. The term renin-angiotensin system (RAS) inhibitor refers to a compound having the ability to down-regulate the conversion of the naturally-occuring plasma glycoprotein angiotensinogen into the N-terminal decapeptide angiotensin I or the subsequent conversion of angiotensin I to the octapeptide angiotensin II. While angiotensin I is known to possess minimal vasoactive properties, angiotensin II is a potent vasoconstrictor which mediates increased systemic vascular resistance with concomitant deleterious impact on various haemodynamic parameters in dysfunctional states. Thus, the renin-angiotensin system is known to be a causative factor in hypertension and congestive heart failure. For a discussion of the mechanisms of action and clinical utilities of various RAS inhibitors see, for example, Drugs, 28, 144–169 (1984) and the references cited therein.

In the practice of the instant invention, any RAS inhibitor may be employed. It is generally preferred, however, that the RAS inhibitor be a compound selected from the group consisting of a renin inhibitor, an angiotensin-converting enzyme (ACE) inhibitor, and an angiotensin II (A-II) antagonist. Especially preferred RAS inhibitors are selected from the group consisting of benazeprilat, captopril, enalapril, lisinopril, losartan, valsartan, irbesartan, candesartan, telmisartan, tasosartan and eprosartan.

The term renin inhibitor refers to a compound having the ability to inhibit the initial, rate-limiting step in the RAS cascade, i.e. the renin-mediated, proteolytic conversion of angiotensinogen into the N-terminal decapeptide angiotensin I, the penultimate precursor to angiotensin II. For a review of various renin inhibitors see, for example, Pharm. Res., 4, 364–374 (1987). A variety of renin inhibitors are, or will be, known to one skilled in the art including those described in U.S. Pat. Nos. 4,814,342, 4,855,303, and 4,895,834, the teachings of which are incorporated herein by reference.

The term angiotensin-converting enzyme (ACE) inhibitor refers to a compound having the ability to inhibit the cleavage of the N-terminal decapeptide angiotensin I to the vasoactive octapeptide angiotensin II. For a review of various ACE inhibitors see, for example, Am. J. Cardiol.66, 7D–13D (1990). A variety of ACE inhibitors are, or will be, known to one skilled in the art including those described in U.S. Pat. Nos. 4,046,889 and 4,374,829, the teachings of which are incorporated herein by reference.

A preferred ACE inhibitor is benazeprilat: (3S)-3-[[(1S)-1-carboxy-3-phenylpropyl]amino]-2,3,4,5-tetrahydro-2-oxo-1H-1-benzazepine-1-acetic acid and the variously substituted 1-carboxymethyl-3-(carboxymethylamino)-2,3,4,5-tetrahydro-1H-[1]benzaepin-2-ones related thereto which are disclosed in U.S. Pat. No. 4,410,520, the disclosure of which is incorporated herein by reference.

Another preferred ACE inhibitor is captopril: 1-[(2S)-3-mercapto-2-methylpropionyl]-L-proline and the various derivatives and compounds related thereto which are disclosed in U.S. Pat. No. 4,105,776, the disclosure of which is incorporated herein by reference.

Other preferred ACE inhibitors are enalapril: 1-[N-[(S)-1-carboxy-3-phenylpropyl]-L-alanyl]-L-proline-1'-ethyl ester and lisinopril: 1-[$N^2$-[(S)-1-carboxy-3-phenylpropyl]-L-lysyl]-L-proline and the various carboxyalkyl dipeptide derivatives and compounds related thereto which are disclosed in U.S. Pat. No. 4,374,829, the disclosure of which is incorporated herein by reference.

The term angiotensin II (A-II) antagonist refers to a compound having the ability to inhibit the vasoactive effects of endogenous angiotensin II by competitive blockade at the angiotensin receptor sites located in vascular smooth muscle and within the adrenal gland. For a detailed review of angiotensin II receptors and the various antagonists thereof see, for example, Pharmacol. Rev. 45, 206–242 (1993). A variety of A-II antagonists are, or will be, known to one skilled in the art including those described in U.S. Pat. Nos. 4,355,040 and 4,880,804, EP 253310, EP 323841, and EP 324377, the teachings of which are incorporated herein by reference.

A preferred A-II antagonist is losartan: 2-butyl-4-chloro-1-[p-(o-1H-tetrazol-5-ylphenyl)benzyl]imidazole-5-methanol, monopotassium salt and the various substituted imidazole derivatives and pharmaceutically acceptable salts related thereto which are disclosed in U.S. Pat. No. 5,138,069, the disclosure of which is incorporated herein by reference.

Another preferred A-II antagonist is valsartan: N-[p-(o-1H-tetrazol-5-yl-phenyl)benzyl]-N-valeryl-L-valine and the various derivatives, pharmaceutically acceptable salts and compounds related thereto which are disclosed in U.S. Pat. No. 5,399,578, the disclosure of which is incorporated herein by reference.

Another preferred A-II antagonist is irbesartan: 2-n-butyl-4-spirocyclopentane-1-(((2'-tetrazol-5-yl)biphenyl-4-yl)-2-imidazolin-5-one and the various derivatives, pharmaceutically acceptable salts and compounds related thereto which are disclosed in U.S. Pat. Nos. 5,270,317 and 5,352,788, the disclosures of which are incorporated herein by reference.

Another preferred A-II antagonist is candesartan: 1-(cyclohexyloxycarbonyloxy)ethyl-2-ethoxy-1-[[2'-(1H-tetrazol-5-yl)biphenyl-4-yl]methyl]benzimidazole-7-carboxylate and the pharmaceutically acceptable salts thereof which are disclosed in U.S. Pat. No. 5,196,444, the disclosure of which is incorporated herein by reference.

Another preferred A-II antagonist is telmisartan: 4'-[[4-methyl-6-(1-methyl-2-benzimidazolyl)-2-propyl-1-benzimidazolyl]methyl]-2-biphenylcarboxylic acid and the various derivatives and compounds related thereto which are disclosed in European Patent Application No. 0 502 314.

Yet another preferred A-II antagonist is tasosartan: 5,8-dihydro-2,4-dimethyl-8-[p-(o-1H-tetrazol-5-ylphenyl)benzyl]pyrido[2,3-d]pyrimidin-7(6H)-one and the pharmaceutically acceptable salts thereof which are disclosed in U.S. Pat. No. 5,149,699, the disclosure of which is incorporated herein by reference.

Still another preferred A-II antagonist is eprosartan: (E)-2-butyl-1-(p-carboxybenzyl)-α-2-thenylimidazole-5-acrylic acid and the pharmaceutically acceptable salts thereof which are disclosed in U.S. Pat. No. 5,185,351, the disclosure of which is incorporated herein by reference.

The preferred synergistic administration of the CRF inhibitor and the RAS antagonist according to this invention can be sequential in time or simultaneous with the simultaneous method being generally preferred. For sequential administration, the CRF inhibitor and the RAS antagonist can be administered in any order. It is generally preferred that such administration be oral. It is even more preferred that the administration be oral and simultaneous. However, if the subject being treated is unable to swallow, or oral absorption is otherwise impaired or undesirable, another route of administration such as suppositories, parenteral (such as subcutaneous, intravenous, intramuscular, intrasternal and infusion techniques), or topical administration will be appropriate. When the CRF inhibitor and the RAS antagonist are administered sequentially, the administration of each can be by the same method or by different methods.

The pharmaceutical compositions of this invention comprise amounts of a CRF antagonist and a RAS inhibitor. Preferred compositions comprise synergistic congestive heart failure-treating or hypertension-treating amounts of a CRF antagonist and a RAS inhibitor. Especially preferred compositions of the instant invention comprise a CRF antagonist of structural formula I or II, or a pharmaceutically acceptable salt thereof, and a RAS inhibitor selected from the group consisting of a renin inhibitor, an angiotensin converting enzyme (ACE) inhibitor, and an angiotensin II (A-II) antagonist. Especially preferred RAS inhibitors are those selected from the group consisting of benazeprilat, captopril, enalapril, lisinopril, losartan, valsartan, irbesartan, candesartan, telmisartan, tasosartan and eprosartan. It is further preferred that the composition comprising the CRF antagonist and the RAS inhibitor be administered in the presence of a pharmaceutically-acceptable carrier or diluent. Suitable pharmaceutical carriers and diluents useful in the administration of the above combinations include inert solid diluents or fillers, sterile aqueous solution and various organic solvents. The pharmaceutical compositions formed by combining the active compounds and the pharmaceutically acceptable carriers or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type can also be employed as fillers in soft and hard filled gelatin capsules. Preferred materials for this include lactose or milk sugar and high molecular weight polyethylene glycols. When aqueous suspensions or elixirs are desired for oral administration, the essential active ingredient(s) therein may be combined with various sweetening or flavoring agents, coloring matter or dyes and, if desired, emulsifying or suspending agents, together with diluents such as water, ethanol, propylene glycol, glycerin and combinations thereof, all of which are pharmaceutically acceptable.

For parenteral administration, solutions of the active compound(s) in sesame or peanut oil, aqueous propylene glycol, or in sterile aqueous solution can be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

For purposes of transdermal (e.g., topical) administration, dilute, sterile, aqueous or partially aqueous solutions (usually in about 0.1% to 5% concentration), otherwise similar to the above parenteral solutions, are employed.

Methods of preparing various pharmaceutical compositions with a certain amount of active ingredient are known, or will be apparent in light of this disclosure, to one skilled in the art. For example, see *Remington's Pharmaceutical Sciences*, Mack Publishing Company, Easton, Pa., 15th Edition (1975).

The dosage(s) of the CRF antagonist and the RAS inhibitor necessary to achieve the desired therapeutic effect according to this invention are within the skill of those who practice in the art of having the benefit of the disclosure herein.

Dosage ranges for certain CRF antagonists have been reported with representative dosages ranging from about 0.1 to 500 mg/kg of the body weight of the patient to be treated. However, some variability in the general dosage range may be required depending upon the age and weight of the patient, the intended route of administration, and the progress and degree of severity of the illness to be treated.

Dosage ranges for certain renin inhibitors have been reported with representative dosages being 0.250 mg/kg to 1.4 mg/kg i.v. and 40 mg/day to 1200 mg/day orally. Dosage ranges for certain ACE inhibitors have been reported with representative dosages of 50 mg/day to 450 mg/day orally and 20 mg/day parenterally. Dosage ranges for certain angiotensin II antagonists have been reported with representative dosages being about 0.5 to 500 mg/kg p.o., preferably 2 to 80 mg/kg p.o., and 3 mg/kg i.v. The dosages to be employed according to this invention may also be varied depending upon the requirements of the subject being treated, the degree of severity of the condition being treated and the compound being administered.

The methods and compositions of the instant invention also have utility in the treatment of congestive heart failure or hypertension in companion animals such as dogs and cats. The administration of the compositions of this invention may be effected orally or parenterally. An amount of a preferred synergistic composition of the invention is administered such that an effective dose is received, usually a daily dose. Conveniently, the medicaments can be carried in the drinking water such that a therapeutic dosage of the agents is ingested with the daily water supply. The agents can be directly metered into drinking water, preferably in the form of a liquid, water-soluble concentrate, such as an aqeuous solution of a water-soluble salt.

Conveniently, the active ingredients can also be added directly to the companion animal's feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and various mineral mixes. A particularly effective carrier is the respective animal feed itself, i.e., a small portion of such feed. The carrier facilitates uniform distribution of the active materials in the finished feed with which the premix is blended. It is important that the compounds be thoroughly blended into the premix and, subsequently, the feed. In this respect, the agents may be dispersed or dissolved in a suitable oily vehicle such as soybean oil, corn oil, cottonseed oil, and the like, or in a volatile organic solvent and then blended with the carrier. It will be appreciated that the proportions of active materials in the concentrate are capable of wide variation since the amount of agent in the finished feed may be adjusted by blending the appropriate proportion of premix with the feed to obtain a desired level of the therapeutic agents.

High potency concentrates may be blended by the feed manufacturer with a proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of compound(s) according to the invention. The mixtures are thoroughly blended by standard procedures, such as in a twin shell blender, to insure homogeneity.

If the supplement is used as a top dressing for the feed, it likewise helps to insure uniformity of distribution of the active ingredient across the top of the dressed feed.

For veterinary uses, both paste and pellet formulations may also be conveniently employed. Paste formulations can be prepared readily by dispersing the active compounds in a pharmaceutically acceptable oil such as peanut oil, sesame oil, corn oil, and the like. Similarly, pellets containing an effective amount of the compounds of the instant invention can be prepared by admixing the compounds of the invention with a suitable diluent such as carbowax, carnuba wax, and the like, and a lubricant, such as magnesium or calcium stearate, can be employed to improve the pelleting process.

Since the instant invention relates to the treatment of congestive heart failure or hypertension with a preferred synergistic combination of active ingredients which may be administered separately, the invention also relates to combining separate pharmaceutical compositions in kit form. A kit, according to this invention, comprises two separate pharmaceutical compositions: a first unit dosage form, comprising a preferably synergistic amount of a CRF antagonist and a pharmaceutically acceptable carrier or diluent and a second unit dosage form comprising a preferably synergistic amount of a RAS inhibitor and a pharmaceutically acceptable carrier or diluent. The kit further comprises a container. The container is used to contain the separate compositions and may comprise, for example, a divided bottle or a divided foil packet, however, the separate compositions may also be contained within a single, undivided container. Normally, the kit will also include directions for the administration of the separate components. The kit form is particularly advantageous when the separate components are preferably administered in different dosage forms (e.g., oral and parenteral), are administered at different dosage levels, or when titration of the individual components of the combination is desired by the prescribing physician.

An example of such a kit is a so-called blister pack. Blister packs are well known in the packaging industry and are being used widely for the packaging of pharmaceutical unit dosage forms (tablets, capsules and the like). Blister packs generally consist of a sheet of relatively rigid material covered with a foil of a preferably transparent plastic material. During the packaging process recesses are formed in the plastic foil. The recesses generally conform to the size and shape of the tablets or capsules to be contained therein. Next, the tablets or capsules are placed in the recesses and the sheet of relatively rigid material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules may be removed from the blister pack by the application of manual pressure on the recesses whereby an opening is formed in the sheet at the place of the recess. The tablet or capsule can then be removed through the formed opening.

It is further desirable to provide a memory aid on the pack, e.g., in the form of numbers or similar indicia next to the tablets or capsules whereby the indicia correspond with the days of the regimen which the dosage form so specified is to be ingested. An additional example of such a memory aid is a calendar printed on the pack, e.g., as follows "First Week, Monday, Tuesday, . . . etc . . . Second Week, Monday, Tuesday, . . ." etc. Other variations will be readily apparent. A "daily dose" can be a single tablet or capsule or multiple tablets or capsules to be ingested on a given day. Also, a daily dose of a CRF antagonist can consist of one tablet or capsule while a daily dose of a RAS inhibitor can consist of multiple tablets or capsules, or vice versa. The memory aid should reflect this.

In another specific embodiment of the invention, a pack designed to dispense the daily doses one at a time in the order of their intended use is provided. Preferably, the pack is equipped with a memory aid, so as to further facilitate compliance with the dosage regimen. An example of such a memory aid is a mechanical counter which indicates the number of daily doses to be dispensed. Another example of such a memory aid is a battery-powered micro-chip memory coupled with a liquid crystal readout, or audible reminder signal which, for example, reads out the date that the last daily dose has been taken and/or reminds the patient when the next dose is to be taken.

Evaluation of the synergistic CRF antagonist—RAS inhibitor combination therapy for treating congestive heart failure and hypertension is performed utilizing the methodology of Sladek, et al., Cardiovascular Research,31, 568–576 (1996).

Adult male Sprague-Dawley rats are anesthetized by intraperitoneal injection of ketamine and sodium pentobarbital. The heart is surgically exposed and the left coronary artery, in experimentally infarcted animals, is occluded by ligation. In sham-operated animals the ligature remains loose. The animals are allowed to recover for a period of three weeks.

Prior to surgery, the treated animals receive a predetermined amount of the test compound and this dosing is continued throughout the recovery period. Three weeks after surgery, the animals from all experimental groups are anesthetized as described previously. Blood pressure in the left (LV) and right ventricles (RV) is measured using a catheter-tip pressure transducer. The catheter is inserted into the left ventricular chamber via the right carotid artery under continuous pressure monitoring. Determinations are recorded after a 15 minute stabilization period. Similarly, a catheter is introduced into the RV via the right jugular vein.

The analog pressure signal is digitized with a sampling frequency of 1 kHz and stored on a computer for later processing. The following parameters are derived: systolic pressure (LVSP, RVSP), left ventricular end-diastolic pressure (LVEDP), developed pressure (LVDevP) and the maximal rates of pressure development $(+dP/dt)_{max}$ and fall $(-dP/dt)_{max}$. In addition, the time constant of relaxation ($\tau$) is calculated on the basis of an experimental model of isovolumetric pressure decay, as the time required for the pressure at $(-dP/dt)_{max}$, to be reduced by 1/e (Mirsky, et al., Prog. Cardiovasc. Dis., 32, 291–318, (1990)). Heart rate is calculated from the left ventricular pressure signal.

The use of this method for assessment of synergy in the treatment of congestive heart failure or hypertension is deemed appropriate where a quantitative dose-response curve for each drug exists. In this instance, a synergistic response is greater than an additive quantitative response obtained with a combination of two agents compared to the same biological response at a particular dose based on the single agent dose-response curve.

What is claimed is:

1. A pharmaceutical composition which comprises amounts of a corticotropin releasing factor antagonist, a renin-angiotensin system inhibitor and a pharmaceutically acceptable carrier or diluent.

2. A pharmaceutical composition of claim 1 which comprises synergistic congestive heart failure-treating or hypertension-treating amounts of a corticotropin releasing factor antagonist, a renin-angiotensin system inhibitor and a pharmaceutically acceptable carrier or diluent.

3. A pharmaceutical composition of claim 2 where said corticotropin releasing factor is a compound having the structural formula

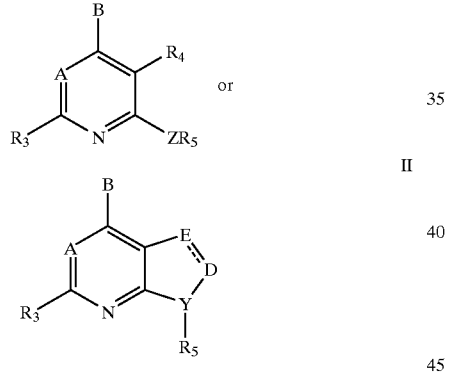

or a pharmaceutically acceptable salt thereof, wherein
the dashed line represents an optional double bond;
A is —$CR_7$ or N;
B is —$NR_1R_2$, —$CR_1R_2R_{11}$, —$C(=CR_1R_{12})R_2$, —$NHCR_{11}R_1R_2$, —$OCR_{11}R_1R_2$; —$SCR_{11}R_1R_2$, —$CR_{11}R_2OR_1$, —$CR_{11}R_2SR_1$, —$C(S)R_2$, —$NHNR_1R_2$, —$CR_2R_{11}NHR_1$ or —$C(O)R_2$;
D is: (i) N or —$CR_{10}$ when a double bond connects E and D and E is —$CR_4$; (ii) —$CR_{10}$ when a double bond connects E and D and E is N; or (iii) —$CR_8R_9$, —$CHR_{10}$, —C=O, —C=S, —C=NH, or —C=$NCH_3$ when a single bond connects E and D;
E is —$CR_4$ or N when a double bond connects E and D, and E is —$CR_4R_6$ or —$NR_6$ when a single bond connects E and D;
Y is N or —CH;
Z is NH, O, S, —N($C_1$–$C_2$ alkyl) or —$CR_{12}R_{13}$, wherein $R_{12}$ and $R_{13}$ are each, independently, hydrogen, trifluoromethyl or methyl, or one of $R_2$ and $R_{13}$ is cyano and the other is hydrogen or methyl;

$R_1$ is hydrogen or $C_1$–$C_6$ alkyl which is optionally substituted with one or two substituents independently selected from hydroxy, cyano, nitro, fluoro, chloro, bromo, iodo, $CF_3$, $C_1$–$C_4$ alkoxy, —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —NH($C_1$–$C_4$ alkyl), —N($C_1$–$C_2$ alkyl)($C_1$–$C_4$ alkyl), —S($C_1$–$C_4$alkyl)CO ($C_1$–$C_4$ alkyl), —NHCO($C_1$–$C_4$ alkyl), —$CO_2$($C_1$–$C_4$ alkyl), —CONH($C_1$–$C_4$ alkyl), —CON($C_1$–$C_4$ alkyl) ($C_1$–$C_2$ alkyl), ($C_1$–$C_4$ alkyl)sulfinyl, ($C_1$–$C_4$ alkyl) sulfonyl, and ($C_1$–$C_4$ alkyl)sulfanyl, and wherein said $C_1$–$C_6$ alkyl, $C_1$–$C_4$ alkoxy and the $C_1$–$C_4$ alkyl moieties in the foregoing $R_1$ groups optionally contain one double or triple bond;

$R_2$ is $C_1$–$C_6$ alkyl, heteroaryl, aryl (heteroaryl)$C_1$–$C_4$ alkyl or (aryl)$C_1$–$C_4$ alkyl wherein said aryl and the aryl moiety of said (aryl)$C_1$–$C_4$ alkyl are selected from the group consisting of phenyl and naphthyl, and said heteroaryl and the heteroaryl moiety of said (heteroaryl)$C_1$–$C_4$ alkyl is selected from the group consisting of thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl; or $R_2$ is $C_3$–$C_8$ cycloalkyl or ($C_3$–$C_8$ cycloalkyl)$C_1$–$C_6$ alkyl, wherein one or two of the ring carbons of said cycloalkyl having at least 4 ring members and the cycloalkyl moiety of said ($C_1$–$C_8$ cycloalkyl)$C_1$–$C_6$ alkyl having at least 4 ring members is optionally replaced with an oxygen or sulfur atom or with —$NR_{14}$ wherein $R_{14}$ is hydrogen or $C_1$–$C_4$ alkyl; and wherein each of the foregoing $R_2$ groups is optionally substituted with from one to three substituents independently selected from chloro, fluoro and $C_1$–$C_4$ alkyl, or with one substituent selected from bromo, iodo, cyano, nitro, $C_1$–$C_6$ alkoxy, —O—CO—($C_1$–$C_4$ alkyl), —O—CO—N($C_1$–$C_4$ alkyl)($C_1$–$C_2$ alkyl), —$CO_2$($C_1$–$C_4$ alkyl), ($C_1$–$C_4$ alkyl)sulfanyl, ($C_1$–$C_4$ alkyl)sulfinyl, and ($C_1$–$C_4$ alkyl)sulfonyl, and wherein said $C_1$–$C_6$ alkyl and the $C_1$–$C_4$ alkyl and $C_1$–$C_6$ alkyl moieties of the foregoing $R_2$ groups optionally contain one carbon—carbon double or triple bond;

or $R^1$ and $R^2$ of said —$NR_1R_2$ and said —$CR_1R_2R_{11}$ are taken together to form a saturated 5 to 8 member ring, wherein said ring optionally contains one or two carbon—carbon double bonds, and wherein one or two of the ring carbons is optionally replaced with a heteroatom selected from O, S and N;

$R_3$ is hydrogen, $C_1$–$C_6$ alkyl, fluoro, chloro, bromo, iodo, hydroxy, amino, SH, —NH($C_1$–$C_4$ alkyl), —N($C_1$–$C_4$ alkyl)($C_1$–$C_2$ alkyl), —$CH_2OH$, —$CH_2OCH_3$, —O($C_1$–$C_4$ alkyl), ($C_1$–$C_4$ alkyl)sulfanyl, ($C_1$–$C_4$ alkyl)sulfonyl, or ($C_1$–$C_4$ alkyl)sulfinyl, wherein said $C_1$–$C_6$ alkyl and the $C_1$–$C_4$ alkyl moieties of the foregoing $R_6$ groups optionally contain one double or triple bond and are optionally substituted with from one to three substituents independently selected from hydroxy, amino, $C_1$–$C_3$ alkoxy, —NH($C_1$–$C_2$ alkyl), —N($C_1$–$C_2$)$_2$, —$NHCOCH_3$, fluoro, chloro and $C_1$–$C_3$ thioalkyl;

$R_4$ is hydrogen, $C_1$–$C_6$ alkyl, fluoro, chloro, bromo, iodo, $C_1$–$C_6$ alkoxy, formyl, trifluoromethoxy, —$CH_2OCH_3$, —$CH_2OCH_2CH_3$, —$CH_2CH_2OCH_3$, —$CH_2CF_3$, $CF_3$, amino, nitro, —NH($C_1$–$C_4$ alkyl), —N($CH_3$)$_2$, —$NHCOCH_3$, —$NHCONHCH_3$, ($C_1$–$C_4$ alkyl) sulfanyl, ($C_1$–$C_4$ alkyl)sulfinyl, ($C_1$–$C_4$ alkyl)sulfonyl, cyano, hydroxy, —CO($C_1$–$C_4$ alkyl), —CHO, or —CO$_2$(C$_1$–C$_4$ alkyl), wherein said C$_1$–C$_6$ alkyl, C$_1$–C$_6$ alkoxy and the C$_1$–C$_4$ alkyl moieties of the foregoing R$_4$ groups optionally contain one double or triple bond and are optionally substituted with one substituent selected from hydroxy, amino, —NHCOCH$_3$, —NH (C$_1$–C$_2$ alkyl), —N(C$_1$–C$_2$ alkyl)$_2$, —CO$_2$(C$_1$–C$_4$ alkyl), —CO(C$_1$–C$_4$ alkyl), C$_1$–C$_3$ alkoxy, (C$_1$–C$_3$ alkyl)sulfanyl, fluoro, chloro, cyano and nitro;

R$_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 3- to 8-membered cycloalkyl or 9- to 12-membered bicycloalkyl, wherein said cycloalkyl and bicycloalkyl optionally contain one or two of O, S or —N—G wherein G is hydrogen, C$_1$–C$_4$ alkyl, C$_1$–C$_4$ alkanoyl, phenyl or benzyl, wherein each of the above R$_5$ groups is optionally substituted with from one to three substituents independently selected from fluoro, chloro, C$_1$–C$_6$ alkyl, C$_1$–C$_6$ alkoxy and trifluoromethyl, or one substituent selected from bromo, iodo, cyano, nitro, amino, —NH(C$_1$–C$_4$ alkyl), —N(C$_1$–C$_4$ alkyl)(C$_1$–C$_2$ alkyl), —CO$_2$(C$_1$–C$_4$ alkyl), —CO(C$_1$–SO$_2$NH(C$_1$–C$_4$ alkyl), —SO$_2$N(C$_1$–C$_4$ alkyl)(C$_1$–C$_2$ alkyl), —SO$_2$NH$_2$, —NHSO$_2$(C$_1$–C$_4$ alkyl), —S(C$_1$–C$_4$ alkyl), and —SO$_2$(C$_1$–C$_4$ alkyl), wherein said C$_1$–C$_4$ alkyl and C$_1$–C$_6$ alkyl moieties of the foregoing R$_5$ groups optionally contain one double or triple bond and are optionally substituted with one or two substituents independently selected from fluoro, chloro, hydroxy, amino, methylamino, dimethylamino and acetyl;

R$_6$ is hydrogen or C$_1$–C$_6$ alkyl, wherein said C$_1$–C$_6$ alkyl is optionally substituted with a single hydroxy, methoxy, ethoxy or fluoro group;

R$_7$ is hydrogen, C$_1$–C$_4$ alkyl, fluoro, chloro, bromo, iodo, cyano, hydroxy, C$_1$–C$_4$ alkoxy, —CO(C$_1$–C$_4$ alkyl), —CO$_2$(C$_1$–C$_4$ alkyl), —OCF$_3$, CF$_3$, —CH$_2$OH, —CH$_2$OCH$_3$ or —CH$_2$OCH$_2$CH$_3$;

R$_8$ and R$_9$ are each, independently, hydrogen, hydroxy, methyl, ethyl, methoxy, or ethoxy;

or R$_8$ and R$_9$ together form an oxo (=O) group;

R$_{10}$ is hydrogen, C$_1$–C$_6$ alkyl, fluoro, chloro, bromo, iodo, C$_1$–C$_6$ alkoxy, formyl, amino, —NH(C$_1$–C$_4$ alkyl), —N(C$_1$–C$_4$ alkyl)(C$_1$–C$_2$ alkyl), —SO$_n$(C$_1$–C$_4$ alkyl), wherein n is 0, 1 or 2, cyano, carboxy, or amido, wherein said C$_1$–C$_6$ alkyl and the C$_1$–C$_4$ alkyl moieties of the foregoing R$_{10}$ groups are optionally substituted with one of hydroxy, trifluoromethyl, amino, carboxy, amido, —NHCO(C$_1$–C$_4$ alkyl), —NH(C$_1$–C$_4$ alkyl), —N(C$_1$–C$_4$ alkyl)(C$_1$–C$_2$ alkyl), —CO$_2$(C$_1$–C$_4$ alkyl), C$_1$–C$_3$ alkoxy, C$_1$–C$_3$ thioalkyl, fluoro chloro, iodo, cyano or nitro; and R$_{11}$ is hydrogen, hydroxy, fluoro, or methoxy; and said renin-angiotensin system inhibitor is selected from the group consisting of a renin inhibitor, an angiotensin-converting enzyme inhibitor and an angiotensin II antagonist.

4. A composition of claim 3 wherein said compound of formula I or II is selected from the group consisting of:

4-(1-ethyl-propoxy)-2,5-dimethyl-6-(2,4,6-trimethyl-benzyl)-pyrimidine;

2-(4-bromo-2,6-dimethyl-phenoxy)-4-(1-ethyl-propoxy)-3,6-dimethyl-pyridine;

2-(4-ethyl-2,6-dimethyl-phenoxy)-4-(1-ethyl-propoxy)-3,6-dimethyl-pyridine;

3-ethyl-4-(1-ethyl-propoxy)-6-methyl-2-(2,4,6-trimethyl-phenoxy)-pyridine;

2-(2,6-dimethyl-4-propyl-phenoxy)-4-(1-ethyl-propoxy)-3,6-dimethyl-pyridine;

4-(1-ethyl-propoxy)-2-(4-methoxy-2,6-dimethyl-phenoxy)-3,6-dimethyl-pyridine;

2-(4-ethoxy-2,6-dimethyl-phenoxy)-4-(1-ethyl-propoxy)-3,6-dimethyl-pyridine;

2-(4-chloro-2,6-dimethyl-phenoxy)-4-(1-ethyl-propoxy)-3,6-dimethyl-pyridine;

4-(1-methoxymethyl-propoxy)-3,6-dimethyl-2-(2,4,6-trimethyl-phenoxy)-pyridine;

[3,6-dimethyl-2-(2,4,6-trimethyl-phenoxy)-pyridin-4-yl]-diethyl-amine;

[3,6-dimethyl-2-(2,4,6-trimethyl-phenoxy)-pyridin-4-yl]-ethyl-propyl-amine;

[2,5-dimethyl-6-(2,4,6-trimethyl-phenoxy)-pyrimidin-4-yl](1-ethyl-propyl)-amine;

butyl-[3,6-dimethyl-2-(2,4,6-trimethyl-phenoxy)-pyridin-4-yl]-ethyl-amine;

4-(1-ethyl-propoxy)-3,6-dimethyl-2-(2,4,6-trimethyl-phenylsulfanyl)-pyridine;

butyl-[2-(4-chloro-2,6-dimethyl-phenoxy)-3,6-dimethyl-pyridin-4-yl]-ethyl-amine;

4-(1-ethyl-propylamino)-6-methyl-2-(2,4,6-trimethyl-phenoxy)-nicotinic acid methyl ester;

[3,6-dimethyl-2-(2,4,6-trimethyl-phenylsulfanyl)-pyridin-4-yl]-ethyl-propyl-amine;

[4-(1-ethyl-propylamino)-6-methyl-2-(2,4,6-trimethyl-phenoxy)-pyridin-3-yl]-methanol;

[2-(4-chloro-2,6-dimethyl-phenoxy)-3,6-dimethyl-pyridin-4-yl]-ethyl-propyl-amine;

1-(ethyl-propyl)-[6-methyl-3-nitro-2-(2,4,6-trimethyl-phenoxy)-pyridin-4-yl]-amine;

N4-(1-ethyl-propyl)-6-methyl-3-nitro-N2-(2,4,6-trimethyl-phenyl)-pyridine-2,4-diamine;

N4-(1-ethyl-propyl)-6-methyl-2-(2,4,6-trimethyl-phenoxy)-pyridine-3,4-diamine;

N4-(1-ethyl-propyl)-6-methyl-N2-(2,4,6-trimethyl-phenyl)-pyridine-2,3,4-triamine;

[3,6-dimethyl-2-(2,4,6-trimethyl-phenoxy)-pyridin-4-yl]-ethyl-(2,2,2-trifluoro-ethyl)-amine;

[3-chloromethyl-6-methyl-2-(2,4,6-trimethyl-phenoxy) pyridin-4-yl]-(1-ethyl-propyl)-amine;

[3,6-dimethyl-2-(2,4,6-trimethyl-phenoxy)-pyridin-4-yl]-(1-ethyl-propyl)-amine;

(1-ethyl-propyl)-[2-methyl-5-nitro-6-(2,4,6-trimethyl-pyridin-3-yloxy)-pyrimidin-4-yl]-amine;

(1-ethyl-propyl)-[3-methoxymethyl-6-methyl-2-(2,4,6-trimethyl-phenoxy)-pyridin-4-yl]-amine;

N-(1-ethyl-propyl)-2-methyl-5-nitro-N-(2,4,6-trimethyl-pyridin-3-yl)-pyrimidine-4,6-diamine;

[2-(4-chloro-2,6-dimethyl-phenoxy)-3,6-dimethyl-pyridin-4-yl]-diethyl-amine;

4-(1-ethyl-propoxy)-3,6-dimethyl-2-(2,4,6-trimethylphenoxy)-pyridine;

butyl-[2,5-dimethyl-7-(2,4,6-tri methyl phenyl)-6,7-dihydro-5H-pyrrolo[2,3-d]pyrimidin-4-yl]-ethyl-amine;

4-(butyl-ethylamino)-2,5-dimethyl-7-(2,4,6trimethylphenyl)-5,7-dihydro-pyrrolo[2,3-d]pyrimidin-6-one;

4-(1-ethylpropoxy)-2,5-dimethyl-6-(2,4,6-trimethylphenoxy)-pyrimidine;

N-butyl-N-ethyl-2,5-dimethyl-N-(2,4,6-trimethylphenyl)-pyrimidine-4,6-diamine;

(1-ethyl-propyl)-[5-methyl-3-(2,4,6-trimethyl-phenyl)-3H-imidazo[4,5-b]pyridin-7-yl]-amine;

[2,5-dimethyl-3-(2,4,6-trimethyl-phenyl)-3H-imidazo[4,5-b]pyridin-7-yl]-(1-ethyl-propyl)-amine;

N4-(1-ethyl-propyl)-6,N3-dimethyl-2-(2,4,6-trimethyl-phenoxy)-pyridine-3,4-diamine;

N4-(1-ethyl-propyl)-6,N3,N3-trimethyl-2-(2,4,6-trimethyl-phenoxy)-pyridine-3,4-diamine;

6-(1-ethyl-propoxy)-2-methyl-N4-(2,4,6-trimethyl-phenyl)-pyrimidine-4,5-diamine;

[4-(1-ethyl-propoxy)-3,6-dimethyl-pyridin-2-yl]-(2,4,6-trimethylphenyl)-amine;

6-(ethyl-propyl-amino)-2,7-dimethyl-9-(2,4,6-trimethylphenyl)-7,9-dihydro-purin-8-one;

butyl-[3,6-dimethyl-1-(2,4,6-trimethylphenyl)-1H-pyrazolo[3,4-b]pyridin-4-yl]-ethylamine;

3,6-dimethyl-4-(tetrahydrofuran-3-yloxy)-1-(2,4,6-trimethylphenyl)-1H-pyrazolo[3,4-b]pyridine

[3,6-dimethyl-1-(2,4,6-trimethylphenyl)-1H-pyrazolo[3,4,b]pyridin-4-yl]-(1-methoxymethylpropyl)-amine;

4-(1-methoxymethylpropoxy)-3,6-dimethyl-1-(2,4,6-trimethylphenyl)-1H-pyrazolo[3,4-b]pyridine;

(1-ethylpropyl)-[3,5,6-trimethyl-1-(2,4,6-trimethylphenyl)-1H-pyrazolo[3,4-b]pyridin-4-yl]-amine;

4-(1-ethylpropoxy)-2,5-dimethyl-7-(2,4,6-trimethylphenyl)-7H-pyrrolo[2,3-b]pyridine;

4-(1-ethylpropoxy)-2,5,6-trimethyl-7-(2,4,6-trimethylphenyl)-7H-pyrrolo[2,3-b]pyridine;

4-(1-ethylpropoxy)-2,5-dimethyl-7-(2,6-dimethyl4-bromophenyl)-7H-pyrrolo[2,3-b]pyridine;

3-{(4-methyl-benzyl)-[3,6-dimethyl-1-(2,4,6-trimethylphenyl)-1 H-pyrazolo[3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo[3,4-d]pyrimidin-4-yl]-amino}-ethanol;

dibutyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfonyl-1-(2,4,6-trichlorophenyl)-1H-pyrazolo[3,4-d]pyrimidin-4-yl]-amine;

butyl-cyclopropylmethyl-[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4 d]pyrimidin-4-yl]-amine;

butyl-ethyl-[6-chloro-3-methylsulfanyl-1-(2,4,6-trichlorophenyl)-1H-pyrazolo[3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-3-methylsulfanyl-1-(2,4,6-trimethylphenyl)-1H-pyrazolo[3,4-d]pyrimidine;

2-[3,6-dimethyl-1-(2,4,6-trimethylphenyl)-1H-pyrazolo[3,4-d]pyrimidin-4-ylamine]-butan-1-ol;

[3,6-dimethyl-1-(2,4,6-trimethylphenyl)-1H-pyrazolo-[3,4-d]pyrimidin-4-yl]-(1-methylpropyl)amine;

4-(1-methoxymethylpropoxy)-3,6-dimethyl-1-(2,4,6-trimethylphenyl)-1H-pyrazolo[3,4-d]pyrimidine;

n-butyl-ethyl-[2,5-dimethyl-7-(2,4,6trimethylphenyl)-7H-pyrrolo[2,3-d]pyrimidin-4-yl]amine;

di-n-propyl-[2,5-dimethyl-7-(2,4,6-trimethylphenyl)-7H-pyrrolo[2,3-d]pyrimidin-4-yl]amine;

ethyl-n-propyl-[2,5-dimethyl-7-(2,4,6-trimethylphenyl)-7H-pyrrolo[2,3-d]pyrimidin-4-yl]amine;

diethyl-2,5-dimethyl-7-(2,4,6-trimethylphenyl)-7H-pyrrolo[2,3-d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine;

2-{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo[2,3-d]pyrimidine;

n-butyl-ethyl-[2,5-dimethyl-7-(2,4-dimethylphenyl)-7H-pyrrolo[2,3-d]pyrimidin-4-yl]amine;

[2,5-dimethyl-7-(2,4,6-trimethylphenyl)-7H-pyrrolo[2,3-d]pyrimidyl4-yl]-(1-ethyl-propyl)amine;

2-[7-(4-bromo-2,6-dimethylphenyl)-2,5-dimethyl-7H-pyrrolo[2,3-d]pyrimidin-4-ylamino]-butan-1-ol;

2-(S)-[7-(4-bromo-2,6-dimethylphenyl)-2,5-dimethyl-7H-pyrrolo[2,3-d]pyrimidin-4-ylamino]-butan-1-ol;

4-(1-ethyl-propoxy)-2,5,6-trimethyl-7-(2,4,6-trimethylphenyl)-7H-pyrrolo[2,3-d]pyrimidine;

4-(1-methoxymethyl-propoxy)-2,5,6-trimethyl-7-(2,4,6-trimethylphenyl)-7H-pyrrolo[2,3-d]pyrimidine;

4-(1-ethyl-butyl)-2,5,6-trimethyl-7-(2,4,6-trimethylphenyl)-7H-pyrrolo-[2,3-d]pyrimidine;

[7-(4-bromo-2,6-dimethyl-phenyl)-2,5-dimethyl-7H-pyrrolo[2,3-d]pyrimidin-4-yl]-(1-methoxymethyl-propyl)-amine;

2-[7-(2-bromo-4,6-dimethyl-phenyl)-2,5-dimethyl-7H-pyrrolo[2,3-d]pyrimidin-4-ylamino]-butan-1-ol;

2-[7-(4-ethyl-2,6-dimethyl-phenyl)-2,5-d dimethyl-7H-pyrrolo[2, 3-d]pyrimidin-4-ylamino]-butan-1-ol;

2-[7-(2-ethyl-4,6-dimethylphenyl)-2,5-dimethyl-7H-pyrrolo[2,3-d]pyrimidin-4-ylamino]-butan-1-ol;

2-[7-(2-fluoromethyl-4,6-dimethylphenyl)-2,5-dimethyl-7H-pyrrolo[2,3-d]pyrimidin-4-ylamino]-butan-1-ol and the pharmaceutically acceptable salts thereof;
and said renin-angiotensin system inhibitor is selected from the group consisting of benazeprilat, captopril, enalapril, lisinopril, losartan, valsartan, irbesartan, candesartan, telmisartan, tasosartan and eprosartan.

5. A kit which comprises an amount of a corticotropin releasing factor antagonist and a pharmaceutically acceptable carrier or diluent in a first unit dosage form, an amount of a renin-angiotensin system inhibitor and a pharmaceutically acceptable carrier or diluent in a second unit dosage form and a container.

6. A kit of claim 5 wherein said corticotropin releasing factor antagonist and said renin-angiotensin system inhibitor are present in synergistic therapeutically effective amounts.

7. A method of treating congestive heart failure which method comprises administering to an animal in need of such treatment a composition according to claim 2 wherein said composition comprises synergistic congestive heart failure treating amounts of a corticotropin releasing factor antagonist, a renin-angiotensin system inhibitor and a pharmaceutically acceptable carrier or diluent.

8. A method of treating hypertension which method comprises administering to an animal in need of such treatment a composition according to claim 2 wherein said composition comprises synergistic hypertension treating amounts of a corticotropin releasing factor antagonist, a renin-angiotensin system inhibitor and a pharmaceutically acceptable carrier or diluent.

9. A method of treating congestive heart failure or hypertension which method comprises administering to an animal in need of such treatment synergistic therapeutically effective amounts of a corticotropin releasing factor antagonist and a renin-angiotensin system inhibitor.

10. A method of claim 9 wherein said renin-angiotensin system inhibitor is selected from the group consisting of a renin inhibitor, an angiotensin-converting enzyme inhibitor, and an angiotensin II antagonist.

11. A method of claim 10 wherein said renin-angiotensin system inhibitor is selected from the group consisting of benazeprilat, captopril, enalapril, lisinopril, losartan, valsartan, irbesartan, candesartan, telmisartan, tasosartan and eprosartan.

12. A method of claim 9 wherein said corticotropin releasing factor antagonist has the structural formula

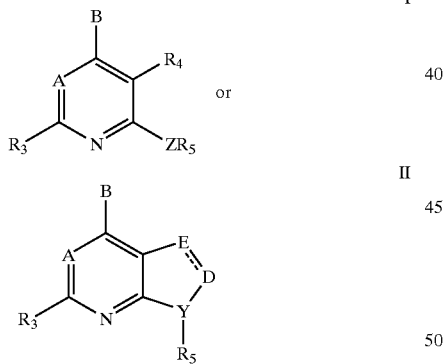

or a pharmaceutically acceptable salt thereof, wherein
the dashed line represents an optional double bond;
A is —CR$_7$ or N;
B is —NR$_1$R$_2$, —CR$_1$R$_2$R$_{11}$, —C(=CR$_1$R$_{12}$)R$_2$, —NHCR$_{11}$R$_1$R$_2$, —OCR$_{11}$R$_1$R$_2$, —SCR$_{11}$R$_1$R$_2$, —CR$_{11}$R$_2$OR$_1$, —CR$_{11}$R$_2$SR$_1$, —C(S)R$_2$, —NHNR$_1$R$_2$, —CR$_2$R$_{11}$NHR$_1$ or —C(O)R$_2$;
D is: (i) N or —CR$_{10}$ when a double bond connects E and D and E is —CR$_4$; (ii) —CR$_{10}$ when a double bond connects E and D and E is N; or (iii) —CR$_8$R$_9$, —CHR$_{10}$, —C=O, —C=S, —C=NH, or —C=NCH$_3$ when a single bond connects E and D;
E is —CR$_4$ or N when a double bond connects E and D, and E is —CR$_4$R$_6$ or —NR$_6$ when a single bond connects E and D;

Y is N or —CH;
Z is NH, O, S, —N(C$_1$–C$_2$ alkyl) or —CR$_{12}$R$_{13}$, wherein R$_{12}$ and R$_{13}$ are each, independently, hydrogen, trifluoromethyl or methyl, or one of R$_{12}$ and R$_{13}$ is cyano and the other is hydrogen or methyl;
R$_1$ is hydrogen or C$_1$–C$_6$ alkyl which is optionally substituted with one or two substituents independently selected from hydroxy, cyano, nitro, fluoro, chloro, bromo, iodo, CF$_3$, C$_1$–C$_4$ alkoxy, —O—CO—(C$_1$–C$_4$ alkyl), —O—CO—NH(C$_1$–C$_4$ alkyl), —O—CO—N (C$_1$–C$_4$ alkyl)(C$_1$–C$_2$ alkyl), —NH(C$_1$–C$_4$ alkyl), —N(C$_1$–C$_2$ alkyl)(C$_1$–C$_4$ alkyl), —S(C$_1$–C$_1$–C$_4$alkyl) CO(C$_1$–C$_4$ alkyl), —NHCO(C$_1$–C$_4$ alkyl), —CO$_2$ (C$_1$–C$_4$ alkyl), —CONH(C$_1$–C$_4$ alkyl), —CON(C$_1$–C$_4$ alkyl)(C$_1$–C$_2$ alkyl), (C$_1$–C$_4$ alkyl)sulfinyl, (C$_1$–C$_4$ alkyl)sulfonyl, and (C$_1$–C$_4$ alkyl)sulfanyl, and wherein said C$_1$–C$_6$ alkyl, C$_1$–C$_4$ alkoxy and the C$_1$–C$_4$ alkyl moieties in the foregoing R$_1$ groups optionally contain one double or triple bond;
R$_2$ is C$_1$–C$_6$ alkyl, heteroaryl, aryl (heteroaryl)C$_1$–C$_4$ alkyl or (aryl)C$_1$–C$_4$ alkyl wherein said aryl and the aryl moiety of said (aryl)C$_1$–C$_4$ alkyl are selected from the group consisting of phenyl and naphthyl, and said heteroaryl and the heteroaryl moiety of said (heteroaryl)C$_1$–C$_4$ alkyl is selected from the group consisting of thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl; or R$^2$ is C$_3$–C$_8$ cycloalkyl or (C$_3$–C$_8$ cycloalkyl)C$_1$–C$_6$ alkyl, wherein one or two of the ring carbons of said cycloalkyl having at least 4 ring members and the cycloalkyl moiety of said (C$_1$–C$_8$ cycloalkyl)C$_1$–C$_6$ alkyl having at least 4 ring members is optionally replaced with an oxygen or sulfur atom or with —NR$_{14}$ wherein R$_{14}$ is hydrogen or C$_1$–C$_4$ alkyl; and wherein each of the foregoing R$_2$ groups is optionally substituted with from one to three substituents independently selected from chloro, fluoro and C$_1$–C$_4$ alkyl, or with one substituent selected from bromo, iodo, cyano, nitro, C$_1$–C$_6$ alkoxy, —O—CO—(C$_1$–C$_4$ alkyl), —O—CO—N(C$_1$–C$_4$ alkyl)(C$_1$–C$_2$ alkyl), —CO$_2$(C$_1$–C$_4$ alkyl), (C$_1$–C$_4$ alkyl)sulfanyl, (C$_1$–C$_4$ alkyl)sulfinyl, and (C$_1$–C$_4$ alkyl)sulfonyl, and wherein said C$_1$–C$_6$ alkyl and the C$_1$–C$_4$ alkyl and C$_1$–C$_6$ alkyl moieties of the foregoing R$_2$ groups optionally contain one carbon—carbon double or triple bond;
or R$^1$ R$^2$ of said —NR$_1$R$_2$ and said —CR$_1$R$_2$R$_{11}$ are taken together to form a saturated 5 to 8 member ring, wherein said ring optionally contains one or two carbon—carbon double bonds, and wherein one or two of the ring carbons is optionally replaced with a heteroatom selected from O, S and N;
R$_3$ is hydrogen, C$_1$–C$_6$ alkyl, fluoro, chloro, bromo, iodo, hydroxy, amino, SH, —NH(C$_1$–C$_4$ alkyl), —N(C$_1$–C$_4$ alkyl)(C$_1$–C$_2$ alkyl), —CH$_2$OH, —CH$_2$OCH$_3$, —O(C$_1$–C$_4$ alkyl), (C$_1$–C$_4$ alkyl)sulfanyl, (C$_1$–C$_4$ alkyl)sulfonyl, or (C$_1$–C$_4$ alkyl)sulfinyl, wherein said C$_1$–C$_6$ alkyl and the C$_1$–C$_4$ alkyl moieties of the foregoing R$_6$ groups optionally contain one double or triple bond and are optionally substituted with from one to three substituents independently selected from hydroxy, amino, C$_1$–C$_3$ alkoxy, —NH(C$_1$–C$_2$ alkyl), —N(C$_1$–C$_2$)$_2$, —NHCOCH$_3$, fluoro, chloro and C$_1$–C$_3$ thioalkyl;
R$_4$ is hydrogen, C$_1$–C$_6$ alkyl, fluoro, chloro, bromo, iodo, C$_1$–C$_6$ alkoxy, formyl, trifluoromethoxy, —CH$_2$OCH$_3$, —CH$_2$OCH$_2$CH$_3$, —CH$_2$CH$_2$OCH$_3$, —CH$_2$CF$_3$, CF$_3$, amino, nitro, —NH(C$_1$–C$_4$ alkyl), —N(CH$_3$)$_2$, —NHCOCH$_3$, —NHCONHCH$_3$, (C$_1$–C$_4$ alkyl)sulfanyl, (C$_1$–C$_4$ alkyl)sulfinyl, (C$_1$–C$_4$ alkyl)sulfonyl, cyano, hydroxy, —CO(C$_1$–C$_4$ alkyl), —CHO, or —CO$_2$(C$_1$–C$_4$ alkyl), wherein said C$_1$–C$_6$ alkyl, C$_1$–C$_6$ alkoxy and the C$_1$–C$_4$ alkyl moieties of the foregoing R$_4$ groups optionally contain one double or triple bond and are optionally substituted with one substituent selected from hydroxy, amino, —NHCOCH$_3$, —NH(C$_1$–C$_2$ alkyl), —N(C$_1$–C$_2$ alkyl)$_2$, —CO$_2$(C$_1$–C$_4$ alkyl), —CO(C$_1$–C$_4$ alkyl), C$_1$–C$_3$ alkoxy, (C$_1$–C$_3$ alkyl)sulfanyl, fluoro, chloro, cyano and nitro;

R$_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 3- to 8-membered cycloalkyl or 9- to 12-membered bicycloalkyl, wherein said cycloalkyl and bicycloalkyl optionally contain one or two of O, S or —N—G wherein G is hydrogen, C$_1$–C$_4$ alkyl, C$_1$–C$_4$ alkanoyl, phenyl or benzyl, wherein each of the above R$_5$ groups is optionally substituted with from one to three substituents independently selected from fluoro, chloro, C$_1$–C$_6$ alkyl, C$_1$–C$_6$ alkoxy and trifluoromethyl, or one substituent selected from bromo, iodo, cyano, nitro, amino, —NH(C$_1$–C$_4$ alkyl), —N(C$_1$–C$_4$ alkyl)(C$_1$–C$_2$ alkyl), —CO$_2$(C$_1$–C$_4$ alkyl), —CO(C$_1$–C$_4$ alkyl), —SO$_2$NH(C$_1$–C$_4$ alkyl), —SO$_2$N(C$_1$–C$_4$ alkyl)(C$_1$–C$_2$ alkyl), —SO$_2$NH$_2$, —NHSO$_2$(C$_1$–C$_4$ alkyl), —S(C$_1$–C$_4$ alkyl), and —SO$_2$(C$_1$–C$_4$ alkyl), wherein said C$_1$–C$_4$ alkyl and C$_1$–C$_6$ alkyl moieties of the foregoing R$_5$ groups optionally contain one double or triple bond and are optionally substituted with one or two substituents independently selected from fluoro, chloro, hydroxy, amino, methylamino, dimethylamino and acetyl;

R$_6$ is hydrogen or C$_1$–C$_6$ alkyl, wherein said C$_1$–C$_6$ alkyl is optionally substituted with a single hydroxy, methoxy, ethoxy or fluoro group;

R$_7$ is hydrogen, C$_1$–C$_4$ alkyl, fluoro, chloro, bromo, iodo, cyano, hydroxy, C$_1$–C$_4$ alkoxy, —CO(C$_1$–C$_4$ alkyl), —CO$_2$(C$_1$–C$_4$ alkyl), —OCF$_3$, CF$_3$, —CH$_2$OH, —CH$_2$OCH$_3$ or —CH$_2$OCH$_2$CH$_3$;

R$_8$ and R$_9$ are each, independently, hydrogen, hydroxy, methyl, ethyl, methoxy, or ethoxy;

or R$_8$ and R$_9$ together form an oxo (=O) group;

R$_{10}$ is hydrogen, C$_1$–C$_6$ alkyl, fluoro, chloro, bromo, iodo, C$_1$–C$_6$ alkoxy, formyl, amino, —NH(C$_1$–C$_4$ alkyl), —N(C$_1$–C$_4$ alkyl)(C$_1$–C$_2$ alkyl), —SO$_n$(C$_1$–C$_4$ alkyl), wherein n is 0, 1 or 2, cyano, carboxy, or amido, wherein said C$_1$–C$_6$ alkyl and the C$_1$–C$_4$ alkyl moieties of the foregoing R$_{10}$ groups are optionally substituted with one of hydroxy, trifluoromethyl, amino, carboxy, amido, —NHCO(C$_1$–C$_4$ alkyl), —NH(C$_1$–C$_4$ alkyl), —N(C$_1$–C$_4$ alkyl)(C$_1$–C$_2$ alkyl), —CO$_2$(C$_1$–C$_4$ alkyl), C$_1$–C$_3$ alkoxy, C$_1$–C$_3$ thioalkyl, fluoro, bromo, chloro, iodo, cyano or nitro; and, R$_{11}$ is hydrogen, hydroxy, fluoro, or methoxy.

13. A method of claim 12 wherein B is —NR$_1$R$_2$, —NHCHR$_1$R$_2$, —CR$_1$R$_2$R$_{11}$, —SCHR$_1$R$_2$ or —OCHR$_1$R$_2$; R$_1$ is C$_1$–C$_6$ alkyl which is optionally substituted with a single hydroxy, fluoro or C$_1$–C$_2$ alkoxy group and optionally contains one carbon—carbon double or triple bond; R$_2$ is benzyl or C$_1$–C$_6$ alkyl which optionally contains one carbon—carbon double or triple bond, wherein said C$_1$–C$_6$ alkyl and the phenyl moiety of said benzyl are optionally substituted with fluoro, C$_1$–C$_2$ alkyl, or C$_1$–C$_2$ alkoxy; and R$_{11}$ is hydrogen or fluoro.

14. A Method of claim 12 wherein R$_2$ is (aryl)C$_1$–C$_4$ alkyl or (heteroaryl)C$_1$–C$_4$ alkyl in which said aryl or heteroaryl moiety is phenyl, thienyl, benzofuranyl, furanyl, benzothienyl, thiazolyl, pyridyl or benzothiazolyl.

15. A method of claim 12 wherein B is NR$_1$R$_2$ or CHR$_1$R$_2$ in which R$_1$ and R$_2$ are taken together with N or CH to form a 5- or 6-membered ring optionally having sulfur, oxygen, or, where B is NR$_1$R$_2$, one more nitrogen in said ring.

16. A method of claim 12 wherein B is —NHCHR$_1$R$_2$ or —OCHR$_1$R$_2$, wherein the CHR$_1$R$_2$ moiety is a 5- or 6-membered ring which optionally contains one oxygen or sulfur.

17. A method of claim 16 wherein B is tetrahydrofuranyl, tetrahydrothiafuranyl, tetrahydrothienyl, thiazolidinyl or cyclopentanyl.

18. A method of claim 12 wherein R$_3$ is methyl, chloro, or methoxy; R$_4$ is methyl, —CH$_2$OH, cyano, trifluoromethoxy, methoxy, trifluoromethyl, chloro, —CO$_2$CH$_3$, —CH$_2$OCH$_3$, —CH$_2$Cl, —CH$_2$F, amino or nitro; R$_6$ is hydrogen, methylsulfinyl, methylsulfanyl, methylsulfonyl, or ethyl; and R$_5$ is phenyl or pyridyl wherein said phenyl or pyridyl is substituted with one substituent independently selected from fluoro, chloro, bromo, iodo, C$_1$–C$_4$ alkoxy, trifluoromethyl, C$_1$–C$_3$ hydroxyalkyl, —CO$_2$(C$_1$–C$_2$ alkyl), (amino)C$_1$–C$_2$ alkyl, —CO(C$_1$–C$_4$ alkyl), and C$_1$–C$_6$ alkyl, wherein said C$_1$–C$_6$ alkyl and said C$_1$–C$_4$ alkyl are optionally substituted with a single hydroxy, or fluoro group and optionally contains one carbon—carbon double or triple bond.

19. A method of claim 12 wherein the compound of formula I or II, is selected from the group consisting of:

4-(1-ethyl-propoxy)-2,5-dimethyl-6-(2,4,6-trimethyl-benzyl)-pyrimidine;

2-(4-bromo-2,6-dimethyl-phenoxy)-4-(1-ethyl-propoxy)-3,6-dimethyl-pyridine;

2-(4-ethyl-2,6-dimethyl-phenoxy)-4-(1-ethyl-propoxy)-3,6-dimethyl-pyridine;

3-ethyl-4-(1-ethyl-propoxy)-6-methyl-2-(2,4,6trimethyl-phenoxy)-pyridine;

2-(2,6-dimethyl-4-propyl-phenoxy)-4-(1-ethyl-propoxy)-3,6-dimethyl-pyridine;

4-(1-ethyl-propoxy)-2-(4-methoxy-2,6-dimethyl-phenoxy)-3,6-dimethyl-pyridine;

2-(4-ethoxy-2,6-dimethyl-phenoxy)-4-(1-ethyl-propoxy)-3,6-dimethyl-pyridine;

2-(4-chloro-2,6-dimethyl-phenoxy)-4-(1-ethyl-propoxy)-3,6-dimethyl-pyridine;

4-(1-methoxymethyl-propoxy)-3,6-dimethyl-2-(2,4,6-trimethyl-phenoxy)-pyridine;

[3,6-dimethyl-2-(2,4,6-trimethyl-phenoxy)-pyridin-4-yl]-diethyl-amine;

[3,6-dimethyl-2-(2,4,6-trimethyl-phenoxy)-pyridin-4-yl]-ethyl-propyl-amine;

[2,5-dimethyl-6-(2,4,6-trimethyl-phenoxy)-pyrimidin-4-yl](1-ethyl-propyl)-amine;

butyl-[3,6-dimethyl-2-(2,4,6-trimethyl-phenoxy)-pyridin-4-yl]-ethyl-amine;

4-(1-ethyl-propoxy)-3,6-dimethyl-2-(2,4,6-trimethyl-phenylsulfanyl)-pyridine;

butyl-[2-(4-chloro-2,6-dimethyl-phenoxy)-3,6-dimethyl-pyridin-4-yl]-ethyl-amine;

4-(1-ethyl-propylamino)-6-methyl-2-(2,4,6-trimethyl-phenoxy)-nicotinic acid methyl ester;

[3,6-dimethyl-2-(2,4,6-trimethyl-phenylsulfanyl)-pyridin-4-yl]-ethyl-propyl-amine;

[4-(1-ethyl-propylamino)-6-methyl-2-(2,4,6-trimethyl-phenoxy)-pyridin-3-yl]-methanol;

[2-(4-chloro-2,6-dimethyl-phenoxy)-3,6-dimethyl-pyridin-4-yl]-ethyl-propyl-amine;

1-(ethyl-propyl)-[6-methyl-3-nitro-2-(2,4,6-trimethyl-phenoxy)-pyridin-4-yl]-amine;

N4-(1-ethyl-propyl)-6-methyl-3-nitro-N2-(2,4,6-trimethyl-phenyl)-pyridine-2,4-diamine;

N4-(1-ethyl-propyl)-6-methyl-2-(2,4,6-trimethyl-phenoxy)-pyridine-3,4-diamine;

N4-(1-ethyl-propyl)-6-methyl-N2-(2,4,6-trimethyl-phenyl)-pyridine-2,3,4-triamine;

[3,6-dimethyl-2-(2,4,6-trimethyl-phenoxy)-pyridin-4-yl]-ethyl-(2,2,2-trifluoro-ethyl)-amine;

[3-chloromethyl-6-methyl-2-(2,4,64trimethyl-phenoxy)pyridin-4-yl]-(1-ethyl-propyl)-amine;

[3,6-dimethyl-2-(2,4,6-trimethyl-phenoxy)-pyridin-4-yl]-(1-ethyl-propyl)-amine;

(1-ethyl-propyl)-[2-methyl-5-nitro-6-(2,4,6-trimethyl-pyridin-3-yloxy)-pyrimidin-4-yl]-amine;

(1-ethyl-propyl)-[3-methoxymethyl-6-methyl-2-(2,4,6-trimethyl-phenoxy)-pyridin-4-yl]-amine;

N-(1-ethyl-propyl)-2-methyl-5-nitro-N-(2,4,6-trimethyl-pyridin-3-yl)-pyrimidine-4,6-diamine;

[2-(4-chloro-2,6-dimethyl-phenoxy)-3,6-dimethyl-pyridin-4-yl]-diethyl-amine;

4-(1-ethyl-propoxy)-3,6-dimethyl-2-(2,4,6-trimethylphenoxy)-pyridine;

butyl-[2,5-dimethyl-7-(2,4,6-trimethylphenyl)-6,7-dihydro-5H-pyrrolo[2,3-d]pyrimidin-4-yl]-ethyl-amine;

4-(butyl-ethylamino)-2,5-dimethyl-7-(2,4,6-trimethylphenyl)-5,7-dihydro-pyrrolo[2,3-d]pyrimidin-6-one;

4-(1-ethylpropoxy)-2,5-dimethyl-6-(2,4,6-trimethylphenoxy)-pyrimidine;

N-butyl-N-ethyl-2,5-dimethyl-N-(2,4,6-trimethylphenyl)-pyrimidine4,6-diamine;

(1-ethyl-propyl)-[5-methyl-3-(2,4,6-trimethyl-phenyl)-3H-imidazo[4,5-b]pyridin-7-yl]-amine;

[2,5-dimethyl-3-(2,4,6-trimethyl-phenyl)-3H-imidazo[4,5-b]pyridin-7-yl]-(1-ethyl-propyl)-amine;

N4-(1-ethyl-propyl)-6,N3-dimethyl-2-(2,4,6-trimethyl-phenoxy)-pyridine-3,4-diamine;

N4-(1-ethyl-propyl)-6,N3,N3-trimethyl-2-(2,4,6-trimethyl-phenoxy)-pyridine-3,4-diamine;

6-(1-ethyl-propoxy)-2-methyl-N4-(2,4,6-trimethyl-phenyl)-pyrimidine-4,5-diamine;

[4-(1-ethyl-propoxy)-3,6-dimethyl-pyridin-2-yl]-(2,4,6-trimethylphenyl)-amine;

6-(ethyl-propyl-amino)-2,7-dimethyl-9-(2,4,6-trimethylphenyl)-7,9-dihydro-purin-8-one; and the pharmaceutically acceptable salts thereof.

20. A method of claim 12 wherein said compound is a compound of formula II in which E and D are connected by a double bond, E is —CR, D is —CR$_{10}$ or N, Y is N, and A is —CR$_7$, or a pharmaceutically acceptable salt thereof.

21. A method of claim 20 wherein said compound is selected from the group consisting of:

butyl-[3,6-dimethyl-1-(2,4,6-trimethylphenyl)-1H-pyrazolo[3,4-b]pyridin-4-yl]-ethylamine;

3,6-dimethyl-4-(tetrahydrofuran-3-yloxy)-1-(2,4,6-trimethylphenyl)-1H-pyrazolo[3,4-b]pyridine

[3,6-dimethyl-1-(2,4,6-trimethylphenyl)-1H-pyrazolo[3,4,b]pyridin-4-yl]-(1-methoxymethylpropyl)-amine;

4-(1-methoxymethylpropoxy)-3,6-dimethyl-1-(2,4,6-trimethylphenyl)-1H-pyrazolo[3,4-b]pyridine;

(1-ethylpropyl)-[3,5,6-trimethyl-1-(2,4,6-trimethylphenyl)-1H-pyrazolo[3,4-b]pyridin-4-yl]-amine;

4-(1-ethylpropoxy)-2,5-dimethyl-7-(2,4,6-trimethylphenyl)-7H-pyrrolo[2,3-b]pyridine;

4-(1-ethylpropoxy)-2,5,6-trimethyl-7-(2,4,6-trimethylphenyl)-7H-pyrrolo[2,3-b]pyridine;

4-(1-ethylpropoxy)-2,5-dimethyl-7-(2,6-dimethyl-4-bromophenyl)-7H-pyrrolo[2,3-b]pyridine; and the pharmaceutically acceptable salts thereof.

22. A method of claim 12 wherein said compound is a compound of formula II in which E and D are connected by a double bond, E is —CR$_4$, and D, Y and A are N, or a pharmaceutically acceptable salt thereof.

23. A method of claim 22 wherein said compound is selected from the group consisting of:

3-{(4-methyl-benzyl)-[3,6-dimethyl-1-(2,4,6-trimethylphenyl)-1H-pyrazolo[3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo[3,4-d]pyrimidin-4-yl]-amino}-ethanol;

dibutyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfonyl-1-(2,4,6-trichlorophenyl)-1H-pyrazolo[3,4-d]pyrimidin-4-yl]-amine;

butyl-cyclopropylmethyl-[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo[3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-]pyrimidin-4-yl]-amine;

4-(1-ethyl-propyl)-6-methyl-3-methylsulfanyl-1-(2,4,6-trimethylphenyl)-1H-pyrazolo[3,4-d]pyrimidine;

2-[3,6-dimethyl-1-(2,4,6-trimethylphenyl)-1H-pyrazolo[3,4-d]pyrimidin-4-ylamine]-butan-1-ol;

[3,6-dimethyl-1-(2,4,6-trimethylphenyl)-1H-pyrazolo-[3,4-d]pyrimidin-4-yl]-(1-methylpropyl)amine;

4-(1-methoxymethylpropoxy)-3,6-dimethyl-1-(2,4,6-trimethylphenyl)-1H-pyrazolo[3,4-d]pyrimidine; and the pharmaceutically acceptable salts thereof.

24. A method of claim 12 wherein said compound is a compound of formula II in which E and D are connected by a double bond, E is —CR$_4$, D is —CR$_{10}$, and Y and A are N, or a pharmaceutically acceptable salt thereof.

25. A method of claim 24 wherein said compound is selected from the group consisting of:

n-butyl-ethyl-[2,5-dimethyl-7-(2,4,6-trimethylphenyl)-7H-pyrrolo[2,3-d]pyrimidin-4-yl]amine;

di-n-propyl-[2,5-dimethyl-7-(2,4,6-trimethylphenyl)-7H-pyrrolo[2,3-d]pyrimidin-4-yl]amine;

ethyl-n-propyl-[2,5-dimethyl-7-(2,4,6-trimethylphenyl)-7H-pyrrolo[2,3-d]pyrimidin-4-yl]amine;

diethyl-2,5-dimethyl-7-(2,4,6-trimethylphenyl)-7H-pyrrolo[2,3-d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine;

2-{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo[2,3-d]pyrimidine;

n-butyl-ethyl-[2,5-dimethyl-7-(2,4-dimethylphenyl)-7H-pyrrolo[2,3-d]pyrimidin-4-yl]amine;

2,5-dimethyl-7-(2,4,6-trimethylphenyl)-7H-pyrrolo[2,3-d]pyrimidyl-4-yl]-(1-ethyl-propyl)amine;

2-[7-(4-bromo-2,6-dimethylphenyl)-2,5-dimethyl-7H-pyrrolo[2,3-d]pyrimidin-4-ylamino]-butan-1-ol;

2-(S)-[7-(4-bromo-2,6-dimethylphenyl)-2,5-dimethyl-7H-pyrrolo[2,3-d]pyrimidin-4-ylamino]-butan-1-ol;

4-(1-ethyl-propoxy)-2,5,6-trimethyl-7-(2,4,6trimethylphenyl)-7H-pyrrolo[2,3-d]pyrimidine;

4-(1-methoxymethyl-propoxy)-2,5,6-trimethyl-7-(2,4,6-trimethylphenyl)-7H-pyrrolo[2,3-d]pyrimidine;

4-(1-ethyl-butyl)-2,5,6-trimethyl-7-(2,4,6-trimethylphenyl)-7H-pyrrolo-[2,3-d]pyrimidine;

[7-(4-bromo-2,6-dimethyl-phenyl-2,5-dimethyl-7H-pyrrolo[2,3-d]pyrimidin-4-yl]-(1-methoxymethyl-propyl)-amine;

2-[7-(2-bromo-4,6-dimethyl-phenyl)-2,5-dimethyl-7H-pyrrolo[2,3-d]pyrimidin-4-ylamino]-butan-1-ol;

2-[7-(4-ethyl-2,6-dimethyl-phenyl)-2,5-dimethyl-7H-pyrrolo[2,3-d]pyrimidin-4-ylamino]-butan-1-ol;

2-[7-(2-ethyl-4,6-dimethylphenyl)-2,5-dimethyl-7H-pyrrolo[2,3-d]pyrimidin-4-ylamino]-butan-1-ol;

2-[7-(2-fluoromethyl-4,6-dimethylphenyl)-2,5-dimethyl-7H-pyrrolo[2,3-d]pyrimidin-4-ylamino]-butan-1-ol; and the pharmaceutically acceptable salts thereof.

26. A method of claim 12 wherein said renin-angiotensin system inhibitor is selected from the group consisting of benazeprilat, captopril, enalapril, lisinopril, losartan, valsartan, irbesartan, candesartan, telmisartan, tasosartan and eprosartan.

* * * * *